（12） United States Patent
Calomeni et al.

(10) Patent No.: US 10,583,005 B2
(45) Date of Patent: Mar. 10, 2020

(54) MEDICAL DEVICE HANDLE

(71) Applicant: BOSTON SCIENTIFIC SCIMED, INC., Maple Grove, MN (US)

(72) Inventors: Michael P. Calomeni, San Jose, CA (US); Takashi H. Ino, San Jose, CA (US); Owen Raybould, Redwood City, CA (US); Randy S. Gamarra, Santa Clara, CA (US); Dwight J. Knab, Jr., Newark, CA (US); Andrew J. H. Backus, Santa Cruz, CA (US); Floriza Q. Escalona, San Jose, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 384 days.

(21) Appl. No.: 15/499,009

(22) Filed: Apr. 27, 2017

(65) Prior Publication Data
US 2017/0325950 A1 Nov. 16, 2017

Related U.S. Application Data

(60) Provisional application No. 62/335,999, filed on May 13, 2016.

(51) Int. Cl.
*A61F 2/24* (2006.01)
*A61F 2/966* (2013.01)
(Continued)

(52) U.S. Cl.
CPC .......... *A61F 2/2427* (2013.01); *A61F 2/2409* (2013.01); *A61F 2/2436* (2013.01);
(Continued)

(58) Field of Classification Search
CPC ........ A61F 2002/9517; A61F 2002/011; A61F 2002/9665; A61F 2/2427; A61F 2/2436; A61F 2/95; A61F 2/966
See application file for complete search history.

(56) References Cited

U.S. PATENT DOCUMENTS 15,192 A 6/1856 Peale
2,682,057 A 6/1954 Lord
(Continued)

FOREIGN PATENT DOCUMENTS

CN 1338951 A 3/2002
DE 19532846 A1 3/1997
(Continued)

OTHER PUBLICATIONS

International Search Report and Written Opinion dated Jul. 24, 2017 for International Application No. PCT/US2017/031863.
(Continued)

*Primary Examiner* — Eric J Rosen
*Assistant Examiner* — Majid Jamialahmadi
(74) *Attorney, Agent, or Firm* — Seager, Tufte & Wickhem LLP

(57) ABSTRACT

A medical device handle may include a handle housing including a cavity disposed within the handle housing. The medical device handle may include a carriage assembly disposed within the cavity and operatively connected to the tubular member and the medical implant, the carriage assembly being longitudinally movable between a distal position and a proximal position by rotation of a control knob with respect to the handle housing, the control knob being disposed around a proximal end of the handle housing. The carriage assembly may include a carriage member, a first sliding member, a second sliding member, and a locking element configured to releasably fix the first sliding member and the second sliding member relative to the carriage member. The locking element may be rotatable relative to the handle housing.

20 Claims, 17 Drawing Sheets

(51) Int. Cl.
*A61F 2/90* (2013.01)
*A61F 2/95* (2013.01)

(52) U.S. Cl.
CPC ............... *A61F 2/2412* (2013.01); *A61F 2/90* (2013.01); *A61F 2002/9505* (2013.01); *A61F 2002/9517* (2013.01); *A61F 2002/9665* (2013.01)

(56) References Cited

U.S. PATENT DOCUMENTS

| | | |
|---|---|---|
| 2,701,559 A | 2/1955 | Cooper |
| 2,832,078 A | 4/1958 | Williams |
| 3,027,637 A | 4/1962 | Seiler |
| 3,099,016 A | 7/1963 | Edwards |
| 3,113,586 A | 12/1963 | Edmark, Jr. |
| 3,130,418 A | 4/1964 | Head et al. |
| 3,143,742 A | 8/1964 | Cromie |
| 3,241,259 A | 3/1966 | McBride |
| 3,334,629 A | 5/1967 | Cohn |
| 3,367,364 A | 2/1968 | Cruz, Jr. et al. |
| 3,409,013 A | 11/1968 | Berry |
| 3,445,916 A | 5/1969 | Schulte |
| 3,540,431 A | 11/1970 | Mobin-Uddin |
| 3,548,417 A | 12/1970 | Kischer et al. |
| 3,570,014 A | 3/1971 | Hancock |
| 3,587,115 A | 6/1971 | Shiley |
| 3,592,184 A | 7/1971 | Watkins et al. |
| 3,628,535 A | 12/1971 | Ostrowsky et al. |
| 3,642,004 A | 2/1972 | Osthagen et al. |
| 3,657,744 A | 4/1972 | Ersek |
| 3,671,979 A | 6/1972 | Moulopoulos |
| 3,714,671 A | 2/1973 | Edwards et al. |
| 3,755,823 A | 9/1973 | Hancock |
| 3,795,246 A | 3/1974 | Sturgeon |
| 3,839,741 A | 10/1974 | Haller |
| 3,868,956 A | 3/1975 | Alfidi et al. |
| 3,874,388 A | 4/1975 | King et al. |
| 3,997,923 A | 12/1976 | Possis |
| 4,035,849 A | 7/1977 | Angell et al. |
| 4,056,854 A | 11/1977 | Boretos et al. |
| 4,106,129 A | 8/1978 | Carpentier et al. |
| 4,222,126 A | 9/1980 | Boretos et al. |
| 4,233,690 A | 11/1980 | Akins |
| 4,265,694 A | 5/1981 | Boretos et al. |
| 4,291,420 A | 9/1981 | Reul |
| 4,297,749 A | 11/1981 | Davis et al. |
| 4,323,358 A | 4/1982 | Lentz et al. |
| 4,326,306 A | 4/1982 | Poler |
| 4,339,831 A | 7/1982 | Johnson |
| 4,343,048 A | 8/1982 | Ross et al. |
| 4,345,340 A | 8/1982 | Rosen |
| 4,373,216 A | 2/1983 | Klawitter |
| 4,406,022 A | 9/1983 | Roy |
| 4,423,809 A | 1/1984 | Mazzocco |
| 4,425,908 A | 1/1984 | Simon |
| 4,470,157 A | 9/1984 | Love |
| 4,484,579 A | 11/1984 | Meno et al. |
| 4,501,030 A | 2/1985 | Lane |
| 4,531,943 A | 7/1985 | Van Tassel et al. |
| 4,535,483 A | 8/1985 | Klawitter et al. |
| 4,574,803 A | 3/1986 | Storz |
| 4,580,568 A | 4/1986 | Gianturco |
| 4,592,340 A | 6/1986 | Boyles |
| 4,602,911 A | 7/1986 | Ahmadi et al. |
| 4,605,407 A | 8/1986 | Black et al. |
| 4,610,688 A | 9/1986 | Silvestrini et al. |
| 4,612,011 A | 9/1986 | Kautzky |
| 4,617,932 A | 10/1986 | Kornberg |
| 4,643,732 A | 2/1987 | Pietsch et al. |
| 4,647,283 A | 3/1987 | Carpentier et al. |
| 4,648,881 A | 3/1987 | Carpentier et al. |
| 4,655,218 A | 4/1987 | Kulik et al. |
| 4,655,771 A | 4/1987 | Wallsten |
| 4,662,885 A | 5/1987 | Dipisa, Jr. |
| 4,665,906 A | 5/1987 | Jervis |
| 4,680,031 A | 7/1987 | Alonso |
| 4,692,164 A | 9/1987 | Dzemeshkevich et al. |
| 4,705,516 A | 11/1987 | Barone et al. |
| 4,710,192 A | 12/1987 | Liotta et al. |
| 4,733,665 A | 3/1988 | Palmaz |
| 4,755,181 A | 7/1988 | Igoe |
| 4,759,758 A | 7/1988 | Gabbay |
| 4,773,420 A | 9/1988 | Green |
| 4,777,951 A | 10/1988 | Cribier et al. |
| 4,787,899 A | 11/1988 | Lazarus |
| 4,787,901 A | 11/1988 | Baykut |
| 4,796,629 A | 1/1989 | Grayzel |
| 4,819,751 A | 4/1989 | Shimada et al. |
| 4,829,990 A | 5/1989 | Thuroff et al. |
| 4,834,755 A | 5/1989 | Silvestrini et al. |
| 4,851,001 A | 7/1989 | Taheri |
| 4,856,516 A | 8/1989 | Hillstead |
| 4,865,600 A | 9/1989 | Carpentier et al. |
| 4,872,874 A | 10/1989 | Taheri |
| 4,873,978 A | 10/1989 | Ginsburg |
| 4,878,495 A | 11/1989 | Grayzel |
| 4,878,906 A | 11/1989 | Lindemann et al. |
| 4,883,458 A | 11/1989 | Shiber |
| 4,885,005 A | 12/1989 | Nashef et al. |
| 4,909,252 A | 3/1990 | Goldberger |
| 4,917,102 A | 4/1990 | Miller et al. |
| 4,922,905 A | 5/1990 | Strecker |
| 4,927,426 A | 5/1990 | Dretler |
| 4,954,126 A | 9/1990 | Wallsten |
| 4,966,604 A | 10/1990 | Reiss |
| 4,969,890 A | 11/1990 | Sugita et al. |
| 4,979,939 A | 12/1990 | Shiber |
| 4,986,830 A | 1/1991 | Owens et al. |
| 4,994,077 A | 2/1991 | Dobben |
| 5,002,556 A | 3/1991 | Ishida et al. |
| 5,002,559 A | 3/1991 | Tower |
| 5,007,896 A | 4/1991 | Shiber |
| 5,026,366 A | 6/1991 | Leckrone |
| 5,032,128 A | 7/1991 | Alonso |
| 5,037,434 A | 8/1991 | Lane |
| 5,047,041 A | 9/1991 | Samuels |
| 5,064,435 A | 11/1991 | Porter |
| 5,080,668 A | 1/1992 | Bolz et al. |
| 5,085,635 A | 2/1992 | Cragg |
| 5,089,015 A | 2/1992 | Ross |
| 5,132,473 A | 7/1992 | Furutaka et al. |
| 5,141,494 A | 8/1992 | Danforth et al. |
| 5,152,771 A | 10/1992 | Sabbaghian et al. |
| 5,159,937 A | 11/1992 | Tremulis |
| 5,161,547 A | 11/1992 | Tower |
| 5,163,953 A | 11/1992 | Vince |
| 5,167,628 A | 12/1992 | Boyles |
| 5,209,741 A | 5/1993 | Spaeth |
| 5,211,086 A | 5/1993 | Shu |
| 5,215,541 A | 6/1993 | Nashef et al. |
| 5,217,483 A | 6/1993 | Tower |
| 5,258,023 A | 11/1993 | Reger |
| 5,258,042 A | 11/1993 | Mehta |
| 5,282,847 A | 2/1994 | Trescony et al. |
| 5,295,958 A | 3/1994 | Shturman |
| 5,332,402 A | 7/1994 | Teitelbaum |
| 5,336,258 A | 8/1994 | Quintero et al. |
| 5,350,398 A | 9/1994 | Pavcnik et al. |
| 5,360,444 A | 11/1994 | Kusuhara |
| 5,370,685 A | 12/1994 | Stevens |
| 5,389,106 A | 2/1995 | Tower |
| 5,397,351 A | 3/1995 | Pavcnik et al. |
| 5,409,019 A | 4/1995 | Wilk |
| 5,411,552 A | 5/1995 | Andersen et al. |
| 5,425,762 A | 6/1995 | Muller |
| 5,431,676 A | 7/1995 | Dubrul et al. |
| 5,443,446 A | 8/1995 | Shturman |
| 5,443,449 A | 8/1995 | Buelna |
| 5,443,477 A | 8/1995 | Marin et al. |
| 5,443,495 A | 8/1995 | Buscemi et al. |
| 5,443,499 A | 8/1995 | Schmitt |
| 5,476,506 A | 12/1995 | Lunn |
| 5,476,510 A | 12/1995 | Eberhardt et al. |

(56) References Cited

U.S. PATENT DOCUMENTS

| | | |
|---|---|---|
| 5,480,423 A | 1/1996 | Ravenscroft et al. |
| 5,480,424 A | 1/1996 | Cox |
| 5,484,440 A | 1/1996 | Allard |
| 5,500,014 A | 3/1996 | Quijano et al. |
| 5,507,767 A | 4/1996 | Maeda et al. |
| 5,534,007 A | 7/1996 | St. Germain et al. |
| 5,545,133 A | 8/1996 | Burns et al. |
| 5,545,209 A | 8/1996 | Roberts et al. |
| 5,545,211 A | 8/1996 | An et al. |
| 5,545,214 A | 8/1996 | Stevens |
| 5,549,665 A | 8/1996 | Vesely et al. |
| 5,554,185 A | 9/1996 | Block et al. |
| 5,571,175 A | 11/1996 | Vanney et al. |
| 5,571,215 A | 11/1996 | Sterman et al. |
| 5,573,520 A | 11/1996 | Schwartz et al. |
| 5,575,818 A | 11/1996 | Pinchuk |
| 5,591,185 A | 1/1997 | Kilmer et al. |
| 5,591,195 A | 1/1997 | Taheri et al. |
| 5,607,464 A | 3/1997 | Trescony et al. |
| 5,609,626 A | 3/1997 | Quijano et al. |
| 5,645,559 A | 7/1997 | Hachtman et al. |
| 5,662,671 A | 9/1997 | Barbut et al. |
| 5,667,523 A | 9/1997 | Bynon et al. |
| 5,674,277 A | 10/1997 | Freitag |
| 5,693,083 A | 12/1997 | Baker et al. |
| 5,693,310 A | 12/1997 | Gries et al. |
| 5,695,498 A | 12/1997 | Tower |
| 5,709,713 A | 1/1998 | Evans et al. |
| 5,713,951 A | 2/1998 | Garrison et al. |
| 5,713,953 A | 2/1998 | Vallana et al. |
| 5,716,370 A | 2/1998 | Williamson, IV et al. |
| 5,716,417 A | 2/1998 | Girard et al. |
| 5,720,391 A | 2/1998 | Dohm et al. |
| 5,725,549 A | 3/1998 | Lam |
| 5,728,068 A | 3/1998 | Leone et al. |
| 5,733,325 A | 3/1998 | Robinson et al. |
| 5,735,842 A | 4/1998 | Krueger et al. |
| 5,749,890 A | 5/1998 | Shaknovich |
| 5,755,783 A | 5/1998 | Stobie et al. |
| 5,756,476 A | 5/1998 | Epstein et al. |
| 5,769,812 A | 6/1998 | Stevens et al. |
| 5,800,456 A | 9/1998 | Maeda et al. |
| 5,800,531 A | 9/1998 | Cosgrove et al. |
| 5,807,405 A | 9/1998 | Vanney et al. |
| 5,817,126 A | 10/1998 | Imran |
| 5,824,041 A | 10/1998 | Lenker et al. |
| 5,824,043 A | 10/1998 | Cottone, Jr. |
| 5,824,053 A | 10/1998 | Khosravi et al. |
| 5,824,055 A | 10/1998 | Spiridigliozzi et al. |
| 5,824,056 A | 10/1998 | Rosenberg |
| 5,824,064 A | 10/1998 | Taheri |
| 5,840,081 A | 11/1998 | Andersen et al. |
| 5,843,158 A | 12/1998 | Lenker et al. |
| 5,855,597 A | 1/1999 | Jayaraman |
| 5,855,601 A | 1/1999 | Bessler et al. |
| 5,855,602 A | 1/1999 | Angell |
| 5,860,966 A | 1/1999 | Tower |
| 5,861,024 A | 1/1999 | Rashidi |
| 5,861,028 A | 1/1999 | Angell |
| 5,868,783 A | 2/1999 | Tower |
| 5,876,419 A | 3/1999 | Carpenter et al. |
| 5,876,448 A | 3/1999 | Thompson et al. |
| 5,885,228 A | 3/1999 | Rosenman et al. |
| 5,888,201 A | 3/1999 | Stinson et al. |
| 5,891,191 A | 4/1999 | Stinson |
| 5,895,399 A | 4/1999 | Barbut et al. |
| 5,906,619 A | 5/1999 | Olson et al. |
| 5,907,893 A | 6/1999 | Zadno-Azizi et al. |
| 5,910,154 A | 6/1999 | Tsugita et al. |
| 5,911,734 A | 6/1999 | Tsugita et al. |
| 5,925,063 A | 7/1999 | Khosravi |
| 5,944,738 A | 8/1999 | Amplatz et al. |
| 5,944,739 A | 8/1999 | Zlock et al. |
| 5,954,766 A | 9/1999 | Zadno-Azizi et al. |
| 5,957,949 A | 9/1999 | Leonhardt et al. |
| 5,968,070 A | 10/1999 | Bley et al. |
| 5,984,957 A | 11/1999 | Laptewicz, Jr. et al. |
| 5,984,959 A | 11/1999 | Robertson et al. |
| 5,993,469 A | 11/1999 | McKenzie et al. |
| 5,997,557 A | 12/1999 | Barbut et al. |
| 6,010,522 A | 1/2000 | Barbut et al. |
| 6,022,370 A | 2/2000 | Tower |
| 6,027,520 A | 2/2000 | Tsugita et al. |
| 6,027,525 A | 2/2000 | Suh et al. |
| 6,042,598 A | 3/2000 | Tsugita et al. |
| 6,042,607 A | 3/2000 | Williamson, IV et al. |
| 6,051,014 A | 4/2000 | Jang |
| 6,059,827 A | 5/2000 | Fenton, Jr. |
| 6,074,418 A | 6/2000 | Buchanan et al. |
| 6,093,203 A | 7/2000 | Uflacker |
| 6,096,074 A | 8/2000 | Pedros |
| 6,123,723 A | 9/2000 | Konya et al. |
| 6,132,473 A | 10/2000 | Williams et al. |
| 6,142,987 A | 11/2000 | Tsugita |
| 6,146,366 A | 11/2000 | Schachar |
| 6,162,245 A | 12/2000 | Jayaraman |
| 6,165,200 A | 12/2000 | Tsugita et al. |
| 6,165,209 A | 12/2000 | Patterson et al. |
| 6,168,579 B1 | 1/2001 | Tsugita |
| 6,168,614 B1 | 1/2001 | Andersen et al. |
| 6,171,327 B1 | 1/2001 | Daniel et al. |
| 6,171,335 B1 | 1/2001 | Wheatley et al. |
| 6,179,859 B1 | 1/2001 | Bates et al. |
| 6,187,016 B1 | 2/2001 | Hedges et al. |
| 6,197,053 B1 | 3/2001 | Cosgrove et al. |
| 6,200,336 B1 | 3/2001 | Pavcnik et al. |
| 6,214,036 B1 | 4/2001 | Letendre et al. |
| 6,221,006 B1 | 4/2001 | Dubrul et al. |
| 6,221,091 B1 | 4/2001 | Khosravi |
| 6,221,096 B1 | 4/2001 | Aiba et al. |
| 6,221,100 B1 | 4/2001 | Strecker |
| 6,231,544 B1 | 5/2001 | Tsuigita et al. |
| 6,231,551 B1 | 5/2001 | Barbut |
| 6,241,757 B1 | 6/2001 | An et al. |
| 6,245,102 B1 | 6/2001 | Jayaraman |
| 6,251,135 B1 | 6/2001 | Stinson et al. |
| 6,258,114 B1 | 7/2001 | Konya et al. |
| 6,258,115 B1 | 7/2001 | Dubrul |
| 6,258,120 B1 | 7/2001 | McKenzie et al. |
| 6,258,129 B1 | 7/2001 | Dybdal et al. |
| 6,264,647 B1 | 7/2001 | Lechot |
| 6,267,783 B1 | 7/2001 | Letendre et al. |
| 6,270,513 B1 | 8/2001 | Tsugita et al. |
| 6,277,555 B1 | 8/2001 | Duran et al. |
| 6,299,637 B1 | 10/2001 | Shaolian et al. |
| 6,302,906 B1 | 10/2001 | Goicoechea et al. |
| 6,309,417 B1 | 10/2001 | Spence et al. |
| 6,319,281 B1 | 11/2001 | Patel |
| 6,327,772 B1 | 12/2001 | Zadno-Azizi et al. |
| 6,336,934 B1 | 1/2002 | Gilson et al. |
| 6,336,937 B1 | 1/2002 | Vonesh et al. |
| 6,338,735 B1 | 1/2002 | Stevens |
| 6,346,116 B1 | 2/2002 | Brooks et al. |
| 6,348,063 B1 | 2/2002 | Yassour et al. |
| 6,352,554 B2 | 3/2002 | De Paulis |
| 6,352,708 B1 | 3/2002 | Duran et al. |
| 6,361,545 B1 | 3/2002 | Macoviak et al. |
| 6,363,938 B2 | 4/2002 | Saadat et al. |
| 6,364,895 B1 | 4/2002 | Greenhalgh |
| 6,371,970 B1 | 4/2002 | Khosravi et al. |
| 6,371,983 B1 | 4/2002 | Lane |
| 6,379,383 B1 | 4/2002 | Palmaz et al. |
| 6,398,807 B1 | 6/2002 | Chouinard et al. |
| 6,402,736 B1 | 6/2002 | Brown |
| 6,409,750 B1 | 6/2002 | Hyodoh et al. |
| 6,416,510 B1 | 7/2002 | Altman et al. |
| 6,425,916 B1 | 7/2002 | Garrison et al. |
| 6,440,164 B1 | 8/2002 | DiMatteo et al. |
| 6,454,799 B1 | 9/2002 | Schreck |
| 6,458,153 B1 | 10/2002 | Bailey et al. |
| 6,461,382 B1 | 10/2002 | Cao |
| 6,468,303 B1 | 10/2002 | Amplatz et al. |
| 6,468,660 B2 | 10/2002 | Ogle et al. |
| 6,475,239 B1 | 11/2002 | Campbell et al. |

(56) References Cited

U.S. PATENT DOCUMENTS

| | | |
|---|---|---|
| 6,482,228 B1 | 11/2002 | Norred |
| 6,485,501 B1 | 11/2002 | Green |
| 6,485,502 B2 | 11/2002 | Don Michael et al. |
| 6,488,704 B1 | 12/2002 | Connelly et al. |
| 6,494,909 B2 | 12/2002 | Greenhalgh |
| 6,503,272 B2 | 1/2003 | Duerig et al. |
| 6,508,833 B2 | 1/2003 | Pavcnik et al. |
| 6,527,800 B1 | 3/2003 | McGuckin, Jr. et al. |
| 6,530,949 B2 | 3/2003 | Konya et al. |
| 6,530,952 B2 | 3/2003 | Vesely |
| 6,537,297 B2 | 3/2003 | Tsugita et al. |
| 6,540,768 B1 | 4/2003 | Diaz et al. |
| 6,562,058 B2 | 5/2003 | Seguin et al. |
| 6,569,196 B1 | 5/2003 | Vesely |
| 6,572,643 B1 | 6/2003 | Gharibadeh |
| 6,585,766 B1 | 7/2003 | Huynh et al. |
| 6,592,546 B1 | 7/2003 | Barbut et al. |
| 6,592,614 B2 | 7/2003 | Lenker et al. |
| 6,605,112 B1 | 8/2003 | Moll et al. |
| 6,610,077 B1 | 8/2003 | Hancock et al. |
| 6,616,682 B2 | 9/2003 | Joergensen et al. |
| 6,622,604 B1 | 9/2003 | Chouinard et al. |
| 6,623,518 B2 | 9/2003 | Thompson et al. |
| 6,623,521 B2 | 9/2003 | Steinke et al. |
| 6,626,892 B1 | 9/2003 | Mayer |
| 6,632,243 B1 | 10/2003 | Zadno-Azizi et al. |
| 6,635,068 B1 | 10/2003 | Dubrul et al. |
| 6,635,079 B2 | 10/2003 | Unsworth et al. |
| 6,652,571 B1 | 11/2003 | White et al. |
| 6,652,578 B2 | 11/2003 | Bailey et al. |
| 6,663,588 B2 | 12/2003 | DuBois et al. |
| 6,663,663 B2 | 12/2003 | Kim et al. |
| 6,669,724 B2 | 12/2003 | Park et al. |
| 6,673,089 B1 | 1/2004 | Yassour et al. |
| 6,673,109 B2 | 1/2004 | Cox |
| 6,676,668 B2 | 1/2004 | Mercereau et al. |
| 6,676,692 B2 | 1/2004 | Rabkin et al. |
| 6,676,698 B2 | 1/2004 | McGuckin, Jr. et al. |
| 6,682,543 B2 | 1/2004 | Barbut et al. |
| 6,682,558 B2 | 1/2004 | Tu et al. |
| 6,682,559 B2 | 1/2004 | Myers et al. |
| 6,685,739 B2 | 2/2004 | DiMatteo et al. |
| 6,689,144 B2 | 2/2004 | Gerberding |
| 6,689,164 B1 | 2/2004 | Seguin |
| 6,692,512 B2 | 2/2004 | Jang |
| 6,695,864 B2 | 2/2004 | Macoviak et al. |
| 6,695,865 B2 | 2/2004 | Boyle et al. |
| 6,702,851 B1 | 3/2004 | Chinn et al. |
| 6,712,842 B1 | 3/2004 | Gifford, III et al. |
| 6,712,843 B2 | 3/2004 | Elliott |
| 6,714,842 B1 | 3/2004 | Ito |
| 6,719,789 B2 | 4/2004 | Cox |
| 6,723,116 B2 | 4/2004 | Taheri |
| 6,730,118 B2 | 5/2004 | Spenser et al. |
| 6,730,377 B2 | 5/2004 | Wang |
| 6,733,525 B2 | 5/2004 | Yang et al. |
| 6,736,846 B2 | 5/2004 | Cox |
| 6,746,412 B1 | 6/2004 | Hill et al. |
| 6,752,828 B2 | 6/2004 | Thornton |
| 6,755,854 B2 | 6/2004 | Gillick et al. |
| 6,758,855 B2 | 7/2004 | Fulton, III et al. |
| 6,764,503 B1 | 7/2004 | Ishimaru |
| 6,764,509 B2 | 7/2004 | Chinn et al. |
| 6,767,345 B2 | 7/2004 | St. Germain et al. |
| 6,769,434 B2 | 8/2004 | Liddicoat et al. |
| 6,773,454 B2 | 8/2004 | Wholey et al. |
| 6,776,791 B1 | 8/2004 | Stallings et al. |
| 6,786,925 B1 | 9/2004 | Schoon et al. |
| 6,790,229 B1 | 9/2004 | Berreklouw |
| 6,790,230 B2 | 9/2004 | Beyersdorf et al. |
| 6,790,237 B2 | 9/2004 | Stinson |
| 6,792,979 B2 | 9/2004 | Konya et al. |
| 6,797,002 B2 | 9/2004 | Spence et al. |
| 6,805,675 B1 | 10/2004 | Gardeski et al. |
| 6,814,746 B2 | 11/2004 | Thompson et al. |
| 6,821,282 B2 | 11/2004 | Perry et al. |
| 6,821,297 B2 | 11/2004 | Snyders |
| 6,830,585 B1 | 12/2004 | Artof et al. |
| 6,837,901 B2 | 1/2005 | Rabkin et al. |
| 6,840,957 B2 | 1/2005 | DiMatteo et al. |
| 6,843,802 B1 | 1/2005 | Villalobos et al. |
| 6,849,085 B2 | 2/2005 | Marton |
| 6,855,160 B1 | 2/2005 | Gambale et al. |
| 6,863,668 B2 | 3/2005 | Gillespie et al. |
| 6,866,650 B2 | 3/2005 | Stevens et al. |
| 6,866,669 B2 | 3/2005 | Buzzard et al. |
| 6,872,223 B2 | 3/2005 | Roberts et al. |
| 6,872,226 B2 | 3/2005 | Cali et al. |
| 6,875,231 B2 | 4/2005 | Anduiza et al. |
| 6,881,220 B2 | 4/2005 | Edwin et al. |
| 6,887,266 B2 | 5/2005 | Williams et al. |
| 6,890,340 B2 | 5/2005 | Duane |
| 6,893,459 B1 | 5/2005 | Macoviak |
| 6,893,460 B2 | 5/2005 | Spenser et al. |
| 6,905,743 B1 | 6/2005 | Chen et al. |
| 6,908,481 B2 | 6/2005 | Cribier |
| 6,911,036 B2 | 6/2005 | Douk et al. |
| 6,911,043 B2 | 6/2005 | Myers et al. |
| 6,936,058 B2 | 8/2005 | Forde et al. |
| 6,936,067 B2 | 8/2005 | Buchanan |
| 6,939,352 B2 | 9/2005 | Buzzard et al. |
| 6,951,571 B1 | 10/2005 | Srivastava |
| 6,953,332 B1 | 10/2005 | Kurk et al. |
| 6,964,673 B2 | 11/2005 | Tsugita et al. |
| 6,969,395 B2 | 11/2005 | Eskuri |
| 6,972,025 B2 | 12/2005 | WasDyke |
| 6,974,464 B2 | 12/2005 | Quijano et al. |
| 6,974,474 B2 | 12/2005 | Pavcnik et al. |
| 6,974,476 B2 | 12/2005 | McGuckin, Jr. et al. |
| 6,979,350 B2 | 12/2005 | Moll et al. |
| 6,984,242 B2 | 1/2006 | Campbell et al. |
| 6,989,027 B2 | 1/2006 | Allen et al. |
| 7,004,176 B2 | 2/2006 | Lau |
| 7,011,681 B2 | 3/2006 | Vesely |
| 7,018,406 B2 | 3/2006 | Seguin et al. |
| 7,025,791 B2 | 4/2006 | Levine et al. |
| 7,037,331 B2 | 5/2006 | Mitelberg et al. |
| 7,041,132 B2 | 5/2006 | Quijano et al. |
| 7,097,658 B2 | 8/2006 | Oktay |
| 7,122,020 B2 | 10/2006 | Mogul |
| 7,125,418 B2 | 10/2006 | Duran et al. |
| 7,141,063 B2 | 11/2006 | White et al. |
| 7,166,097 B2 | 1/2007 | Barbut |
| 7,175,653 B2 | 2/2007 | Gaber |
| 7,175,654 B2 | 2/2007 | Bonsignore et al. |
| 7,175,656 B2 | 2/2007 | Khairkhahan |
| 7,189,258 B2 | 3/2007 | Johnson et al. |
| 7,191,018 B2 | 3/2007 | Gielen et al. |
| 7,201,772 B2 | 4/2007 | Schwammenthal et al. |
| 7,235,093 B2 | 6/2007 | Gregorich |
| 7,258,696 B2 | 8/2007 | Rabkin et al. |
| 7,267,686 B2 | 9/2007 | DiMatteo et al. |
| 7,276,078 B2 | 10/2007 | Spenser et al. |
| 7,318,278 B2 | 1/2008 | Zhang et al. |
| 7,322,932 B2 | 1/2008 | Xie et al. |
| 7,326,236 B2 | 2/2008 | Andreas et al. |
| 7,329,279 B2 | 2/2008 | Haug et al. |
| 7,374,560 B2 | 5/2008 | Ressemann et al. |
| 7,381,219 B2 | 6/2008 | Salahieh et al. |
| 7,381,220 B2 | 6/2008 | Macoviak et al. |
| 7,399,315 B2 | 7/2008 | Iobbi |
| 7,445,631 B2 | 11/2008 | Salahieh et al. |
| 7,470,285 B2 | 12/2008 | Nugent et al. |
| 7,491,232 B2 | 2/2009 | Bolduc et al. |
| 7,510,574 B2 | 3/2009 | Lê et al. |
| 7,524,330 B2 | 4/2009 | Berreklouw |
| 7,530,995 B2 | 5/2009 | Quijano et al. |
| 7,544,206 B2 | 6/2009 | Cohn |
| 7,622,276 B2 | 11/2009 | Cunanan et al. |
| 7,628,803 B2 | 12/2009 | Pavcnik et al. |
| 7,632,298 B2 | 12/2009 | Hijikerna et al. |
| 7,674,282 B2 | 3/2010 | Wu et al. |
| 7,712,606 B2 | 5/2010 | Salahieh et al. |
| 7,722,638 B2 | 5/2010 | Deyette, Jr. et al. |

(56) References Cited

U.S. PATENT DOCUMENTS

| | | |
|---|---|---|
| 7,722,662 B2 | 5/2010 | Steinke et al. |
| 7,722,666 B2 | 5/2010 | Lafontaine |
| 7,736,388 B2 | 6/2010 | Goldfarb et al. |
| 7,748,389 B2 | 7/2010 | Salahieh et al. |
| 7,758,625 B2 | 7/2010 | Wu et al. |
| 7,780,725 B2 | 8/2010 | Haug et al. |
| 7,799,065 B2 | 9/2010 | Pappas |
| 7,803,185 B2 | 9/2010 | Gabbay |
| 7,824,442 B2 | 11/2010 | Salahieh et al. |
| 7,824,443 B2 | 11/2010 | Salahieh et al. |
| 7,833,262 B2 | 11/2010 | McGuckin, Jr. et al. |
| 7,846,204 B2 | 12/2010 | Letac et al. |
| 7,892,292 B2 | 2/2011 | Stack et al. |
| 7,918,880 B2 | 4/2011 | Austin |
| 7,938,851 B2 | 5/2011 | Olson et al. |
| 7,959,666 B2 | 6/2011 | Salahieh et al. |
| 7,959,672 B2 | 6/2011 | Salahieh et al. |
| 7,988,724 B2 | 8/2011 | Salahieh et al. |
| 8,011,067 B2 | 9/2011 | Thompson |
| 8,048,153 B2 | 11/2011 | Salahieh et al. |
| 8,052,749 B2 | 11/2011 | Salahieh et al. |
| 8,157,146 B2 | 4/2012 | Edoga et al. |
| 8,172,863 B2 | 5/2012 | Robinson et al. |
| 8,182,528 B2 | 5/2012 | Salahieh et al. |
| 8,192,351 B2 | 6/2012 | Fishler et al. |
| 8,226,710 B2 | 7/2012 | Nguyen et al. |
| 8,231,670 B2 | 7/2012 | Salahieh et al. |
| 8,236,049 B2 | 8/2012 | Rowe et al. |
| 8,241,344 B2 | 8/2012 | Kusleika et al. |
| 8,246,678 B2 | 8/2012 | Salahieh et al. |
| 8,252,051 B2 | 8/2012 | Chau et al. |
| 8,252,052 B2 | 8/2012 | Salahieh et al. |
| 8,308,798 B2 | 11/2012 | Pintor et al. |
| 8,323,335 B2 | 12/2012 | Rowe et al. |
| 8,328,868 B2 | 12/2012 | Paul et al. |
| 8,343,213 B2 | 1/2013 | Salahieh et al. |
| 8,376,865 B2 | 2/2013 | Forster et al. |
| 8,377,117 B2 | 2/2013 | Keidar et al. |
| 8,398,708 B2 | 3/2013 | Meiri et al. |
| 8,579,962 B2 | 11/2013 | Salahieh et al. |
| 8,603,160 B2 | 12/2013 | Salahieh et al. |
| 8,617,236 B2 | 12/2013 | Paul et al. |
| 8,623,076 B2 | 1/2014 | Salahieh et al. |
| 8,623,078 B2 | 1/2014 | Salahieh et al. |
| 8,663,303 B2 | 3/2014 | Horvath et al. |
| 8,668,733 B2 | 3/2014 | Haug et al. |
| 8,721,702 B2 | 5/2014 | Romoda et al. |
| 8,808,350 B2 | 8/2014 | Schreck et al. |
| 8,828,078 B2 | 9/2014 | Salahieh et al. |
| 8,840,662 B2 | 9/2014 | Salahieh et al. |
| 8,840,663 B2 | 9/2014 | Salahieh et al. |
| 8,858,620 B2 | 10/2014 | Salahieh et al. |
| 8,951,243 B2 | 2/2015 | Crisostomo et al. |
| 9,131,926 B2 | 9/2015 | Crisostomo et al. |
| 2001/0002445 A1 | 5/2001 | Vesely |
| 2001/0007956 A1 | 7/2001 | Letac et al. |
| 2001/0010017 A1 | 7/2001 | Letac et al. |
| 2001/0021872 A1 | 9/2001 | Bailey et al. |
| 2001/0025196 A1 | 9/2001 | Chinn et al. |
| 2001/0032013 A1 | 10/2001 | Marton |
| 2001/0039450 A1 | 11/2001 | Pavcnik et al. |
| 2001/0041928 A1 | 11/2001 | Pavcnik et al. |
| 2001/0041930 A1 | 11/2001 | Globerman et al. |
| 2001/0044634 A1 | 11/2001 | Don Michael et al. |
| 2001/0044652 A1 | 11/2001 | Moore |
| 2001/0044656 A1 | 11/2001 | Williamson, IV et al. |
| 2002/0002396 A1 | 1/2002 | Fulkerson |
| 2002/0010489 A1 | 1/2002 | Grayzel et al. |
| 2002/0026233 A1 | 2/2002 | Shaknovich |
| 2002/0029014 A1 | 3/2002 | Jayaraman |
| 2002/0029981 A1 | 3/2002 | Nigam |
| 2002/0032480 A1 | 3/2002 | Spence et al. |
| 2002/0032481 A1 | 3/2002 | Gabbay |
| 2002/0042651 A1 | 4/2002 | Liddicoat et al. |
| 2002/0052651 A1 | 5/2002 | Myers et al. |
| 2002/0055767 A1 | 5/2002 | Forde et al. |
| 2002/0055769 A1 | 5/2002 | Wang |
| 2002/0058995 A1 | 5/2002 | Stevens |
| 2002/0077696 A1 | 6/2002 | Zadno-Azizi et al. |
| 2002/0082609 A1 | 6/2002 | Green |
| 2002/0095173 A1 | 7/2002 | Mazzocchi et al. |
| 2002/0095209 A1 | 7/2002 | Zadno-Azizi et al. |
| 2002/0111674 A1 | 8/2002 | Chouinard et al. |
| 2002/0120328 A1 | 8/2002 | Pathak et al. |
| 2002/0123802 A1 | 9/2002 | Snyders |
| 2002/0138138 A1 | 9/2002 | Yang |
| 2002/0151970 A1 | 10/2002 | Garrison et al. |
| 2002/0161390 A1 | 10/2002 | Mouw |
| 2002/0161392 A1 | 10/2002 | Dubrul |
| 2002/0161394 A1 | 10/2002 | Macoviak et al. |
| 2002/0165576 A1 | 11/2002 | Boyle et al. |
| 2002/0177766 A1 | 11/2002 | Mogul |
| 2002/0183781 A1 | 12/2002 | Casey et al. |
| 2002/0188341 A1 | 12/2002 | Elliott |
| 2002/0188344 A1 | 12/2002 | Bolea et al. |
| 2002/0193871 A1 | 12/2002 | Beyersdorf et al. |
| 2003/0014104 A1 | 1/2003 | Cribier |
| 2003/0023303 A1 | 1/2003 | Palmaz et al. |
| 2003/0028247 A1 | 2/2003 | Cali |
| 2003/0036791 A1 | 2/2003 | Philipp et al. |
| 2003/0040736 A1 | 2/2003 | Stevens et al. |
| 2003/0040771 A1 | 2/2003 | Hyodoh et al. |
| 2003/0040772 A1 | 2/2003 | Hyodoh et al. |
| 2003/0040791 A1 | 2/2003 | Oktay |
| 2003/0040792 A1 | 2/2003 | Gabbay |
| 2003/0050694 A1 | 3/2003 | Yang et al. |
| 2003/0055495 A1 | 3/2003 | Pease et al. |
| 2003/0057156 A1 | 3/2003 | Peterson et al. |
| 2003/0060844 A1 | 3/2003 | Borillo et al. |
| 2003/0069492 A1 | 4/2003 | Abrams et al. |
| 2003/0069646 A1 | 4/2003 | Stinson |
| 2003/0070944 A1 | 4/2003 | Nigam |
| 2003/0100918 A1 | 5/2003 | Duane |
| 2003/0100919 A1 | 5/2003 | Hopkins et al. |
| 2003/0109924 A1 | 6/2003 | Cribier |
| 2003/0109930 A1 | 6/2003 | Bluni et al. |
| 2003/0114912 A1 | 6/2003 | Sequin et al. |
| 2003/0114913 A1 | 6/2003 | Spenser et al. |
| 2003/0125795 A1 | 7/2003 | Pavcnik et al. |
| 2003/0130729 A1 | 7/2003 | Paniagua et al. |
| 2003/0135257 A1 | 7/2003 | Taheri |
| 2003/0144732 A1 | 7/2003 | Cosgrove et al. |
| 2003/0149475 A1 | 8/2003 | Hyodoh et al. |
| 2003/0149476 A1 | 8/2003 | Damm et al. |
| 2003/0149478 A1 | 8/2003 | Figulla et al. |
| 2003/0153974 A1 | 8/2003 | Spenser et al. |
| 2003/0171803 A1 | 9/2003 | Shimon |
| 2003/0176884 A1 | 9/2003 | Berrada et al. |
| 2003/0181850 A1 | 9/2003 | Diamond et al. |
| 2003/0187495 A1 | 10/2003 | Cully et al. |
| 2003/0191516 A1 | 10/2003 | Weldon et al. |
| 2003/0195609 A1 | 10/2003 | Berenstein et al. |
| 2003/0199759 A1 | 10/2003 | Richard |
| 2003/0199913 A1 | 10/2003 | Dubrul et al. |
| 2003/0199971 A1 | 10/2003 | Tower et al. |
| 2003/0199972 A1 | 10/2003 | Zadno-Azizi et al. |
| 2003/0208224 A1 | 11/2003 | Broome |
| 2003/0212429 A1 | 11/2003 | Keegan et al. |
| 2003/0212452 A1 | 11/2003 | Zadno-Azizi et al. |
| 2003/0212454 A1 | 11/2003 | Scott et al. |
| 2003/0216774 A1 | 11/2003 | Larson |
| 2003/0225445 A1 | 12/2003 | Derus et al. |
| 2003/0229390 A1 | 12/2003 | Ashton et al. |
| 2003/0233117 A1 | 12/2003 | Adams et al. |
| 2004/0019374 A1 | 1/2004 | Hojeibane et al. |
| 2004/0034411 A1 | 2/2004 | Quijano et al. |
| 2004/0039436 A1 | 2/2004 | Spenser et al. |
| 2004/0049224 A1 | 3/2004 | Buehlmann et al. |
| 2004/0049226 A1 | 3/2004 | Keegan et al. |
| 2004/0049262 A1 | 3/2004 | Obermiller et al. |
| 2004/0049266 A1 | 3/2004 | Anduiza et al. |
| 2004/0059409 A1 | 3/2004 | Stenzel |
| 2004/0073198 A1 | 4/2004 | Gilson et al. |
| 2004/0082904 A1 | 4/2004 | Houde et al. |

(56) References Cited

U.S. PATENT DOCUMENTS

| | | |
|---|---|---|
| 2004/0082967 A1 | 4/2004 | Broome et al. |
| 2004/0087982 A1 | 5/2004 | Eskuri |
| 2004/0088045 A1 | 5/2004 | Cox |
| 2004/0093016 A1 | 5/2004 | Root et al. |
| 2004/0093060 A1 | 5/2004 | Seguin et al. |
| 2004/0097788 A1 | 5/2004 | Mourlas et al. |
| 2004/0098022 A1 | 5/2004 | Barone |
| 2004/0098098 A1 | 5/2004 | McGuckin, Jr. et al. |
| 2004/0098099 A1 | 5/2004 | McCullagh et al. |
| 2004/0098112 A1 | 5/2004 | DiMatteo et al. |
| 2004/0107004 A1 | 6/2004 | Levine et al. |
| 2004/0111096 A1 | 6/2004 | Tu et al. |
| 2004/0116951 A1 | 6/2004 | Rosengart |
| 2004/0117004 A1 | 6/2004 | Osborne et al. |
| 2004/0117009 A1 | 6/2004 | Cali et al. |
| 2004/0122468 A1 | 6/2004 | Yodfat et al. |
| 2004/0122516 A1 | 6/2004 | Fogarty et al. |
| 2004/0127936 A1 | 7/2004 | Salahieh et al. |
| 2004/0127979 A1 | 7/2004 | Wilson et al. |
| 2004/0133274 A1 | 7/2004 | Webler et al. |
| 2004/0138694 A1 | 7/2004 | Tran et al. |
| 2004/0138742 A1 | 7/2004 | Myers et al. |
| 2004/0138743 A1 | 7/2004 | Myers et al. |
| 2004/0148018 A1 | 7/2004 | Carpentier et al. |
| 2004/0148021 A1 | 7/2004 | Cartledge et al. |
| 2004/0153094 A1 | 8/2004 | Dunfee et al. |
| 2004/0158277 A1 | 8/2004 | Lowe et al. |
| 2004/0167565 A1 | 8/2004 | Beulke et al. |
| 2004/0167620 A1 | 8/2004 | Ortiz et al. |
| 2004/0181140 A1 | 9/2004 | Falwell et al. |
| 2004/0186558 A1 | 9/2004 | Pavcnik et al. |
| 2004/0186563 A1 | 9/2004 | Lobbi |
| 2004/0193261 A1 | 9/2004 | Berreklouw |
| 2004/0199245 A1 | 10/2004 | Lauterjung |
| 2004/0204755 A1 | 10/2004 | Robin |
| 2004/0210304 A1 | 10/2004 | Seguin et al. |
| 2004/0210306 A1 | 10/2004 | Quijano et al. |
| 2004/0210307 A1 | 10/2004 | Khairkhahan |
| 2004/0215331 A1 | 10/2004 | Chew et al. |
| 2004/0215333 A1 | 10/2004 | Duran et al. |
| 2004/0215339 A1 | 10/2004 | Drasler et al. |
| 2004/0220655 A1 | 11/2004 | Swanson et al. |
| 2004/0225321 A1 | 11/2004 | Krolik et al. |
| 2004/0225353 A1 | 11/2004 | McGuckin, Jr. et al. |
| 2004/0225354 A1 | 11/2004 | Allen et al. |
| 2004/0225355 A1 | 11/2004 | Stevens |
| 2004/0243221 A1 | 12/2004 | Fawzi et al. |
| 2004/0254636 A1 | 12/2004 | Flagle et al. |
| 2004/0260390 A1 | 12/2004 | Sarac et al. |
| 2005/0010287 A1 | 1/2005 | Macoviak et al. |
| 2005/0021136 A1 | 1/2005 | Xie et al. |
| 2005/0033398 A1 | 2/2005 | Seguin |
| 2005/0033402 A1 | 2/2005 | Cully et al. |
| 2005/0043711 A1 | 2/2005 | Corcoran et al. |
| 2005/0043757 A1 | 2/2005 | Arad et al. |
| 2005/0043790 A1 | 2/2005 | Seguin |
| 2005/0049692 A1 | 3/2005 | Numamoto et al. |
| 2005/0049696 A1 | 3/2005 | Siess et al. |
| 2005/0055088 A1 | 3/2005 | Liddicoat et al. |
| 2005/0060016 A1 | 3/2005 | Wu et al. |
| 2005/0060029 A1 | 3/2005 | Le et al. |
| 2005/0065594 A1 | 3/2005 | DiMatteo et al. |
| 2005/0075584 A1 | 4/2005 | Cali |
| 2005/0075662 A1 | 4/2005 | Pedersen et al. |
| 2005/0075712 A1 | 4/2005 | Biancucci et al. |
| 2005/0075717 A1 | 4/2005 | Nguyen et al. |
| 2005/0075719 A1 | 4/2005 | Bergheim |
| 2005/0075724 A1 | 4/2005 | Svanidze et al. |
| 2005/0075730 A1 | 4/2005 | Myers et al. |
| 2005/0075731 A1 | 4/2005 | Artof et al. |
| 2005/0085841 A1 | 4/2005 | Eversull et al. |
| 2005/0085842 A1 | 4/2005 | Eversull et al. |
| 2005/0085843 A1 | 4/2005 | Opolski et al. |
| 2005/0085890 A1 | 4/2005 | Rasmussen et al. |
| 2005/0090846 A1 | 4/2005 | Pedersen et al. |
| 2005/0090890 A1 | 4/2005 | Wu et al. |
| 2005/0096692 A1 | 5/2005 | Linder et al. |
| 2005/0096734 A1 | 5/2005 | Majercak et al. |
| 2005/0096735 A1 | 5/2005 | Hojeibane et al. |
| 2005/0096736 A1 | 5/2005 | Osse et al. |
| 2005/0096738 A1 | 5/2005 | Cali et al. |
| 2005/0100580 A1 | 5/2005 | Osborne et al. |
| 2005/0107822 A1 | 5/2005 | Wasdyke |
| 2005/0113910 A1 | 5/2005 | Paniagua et al. |
| 2005/0131438 A1 | 6/2005 | Cohn |
| 2005/0137683 A1 | 6/2005 | Hezi-Yamit et al. |
| 2005/0137686 A1 | 6/2005 | Salahieh et al. |
| 2005/0137687 A1 | 6/2005 | Salahieh et al. |
| 2005/0137688 A1 | 6/2005 | Salahieh et al. |
| 2005/0137689 A1 | 6/2005 | Salahieh et al. |
| 2005/0137690 A1 | 6/2005 | Salahieh et al. |
| 2005/0137691 A1 | 6/2005 | Salahieh et al. |
| 2005/0137692 A1 | 6/2005 | Haug et al. |
| 2005/0137693 A1 | 6/2005 | Haug et al. |
| 2005/0137694 A1 | 6/2005 | Haug et al. |
| 2005/0137695 A1 | 6/2005 | Salahieh et al. |
| 2005/0137696 A1 | 6/2005 | Salahieh et al. |
| 2005/0137697 A1 | 6/2005 | Salahieh et al. |
| 2005/0137698 A1 | 6/2005 | Salahieh et al. |
| 2005/0137699 A1 | 6/2005 | Salahieh et al. |
| 2005/0137701 A1 | 6/2005 | Salahieh et al. |
| 2005/0137702 A1 | 6/2005 | Haug et al. |
| 2005/0143807 A1 | 6/2005 | Pavcnik et al. |
| 2005/0143809 A1 | 6/2005 | Salahieh et al. |
| 2005/0149159 A1 | 7/2005 | Andreas et al. |
| 2005/0165352 A1 | 7/2005 | Henry et al. |
| 2005/0165477 A1 | 7/2005 | Anduiza et al. |
| 2005/0165479 A1 | 7/2005 | Drews et al. |
| 2005/0182486 A1 | 8/2005 | Gabbay |
| 2005/0197694 A1 | 9/2005 | Pai et al. |
| 2005/0197695 A1 | 9/2005 | Stacchino et al. |
| 2005/0203549 A1 | 9/2005 | Realyvasquez |
| 2005/0203614 A1 | 9/2005 | Forster et al. |
| 2005/0203615 A1 | 9/2005 | Forster et al. |
| 2005/0203616 A1 | 9/2005 | Cribier |
| 2005/0203617 A1 | 9/2005 | Forster et al. |
| 2005/0203618 A1 | 9/2005 | Sharkawy et al. |
| 2005/0209580 A1 | 9/2005 | Freyman |
| 2005/0228472 A1 | 10/2005 | Case et al. |
| 2005/0228495 A1 | 10/2005 | Macoviak |
| 2005/0234546 A1 | 10/2005 | Nugent et al. |
| 2005/0240200 A1 | 10/2005 | Bergheim |
| 2005/0240262 A1 | 10/2005 | White |
| 2005/0251250 A1 | 11/2005 | Verhoeven et al. |
| 2005/0251251 A1 | 11/2005 | Cribier |
| 2005/0261759 A1 | 11/2005 | Lambrecht et al. |
| 2005/0267560 A1 | 12/2005 | Bates |
| 2005/0283231 A1 | 12/2005 | Haug et al. |
| 2005/0283962 A1 | 12/2005 | Boudjemline |
| 2006/0004439 A1 | 1/2006 | Spenser et al. |
| 2006/0004442 A1 | 1/2006 | Spenser et al. |
| 2006/0015168 A1 | 1/2006 | Gunderson |
| 2006/0058872 A1 | 3/2006 | Salahieh et al. |
| 2006/0149360 A1 | 7/2006 | Schwammenthal et al. |
| 2006/0155312 A1 | 7/2006 | Levine et al. |
| 2006/0161249 A1 | 7/2006 | Realyvasquez et al. |
| 2006/0173524 A1 | 8/2006 | Salahieh et al. |
| 2006/0195183 A1 | 8/2006 | Navia et al. |
| 2006/0253191 A1 | 11/2006 | Salahieh et al. |
| 2006/0259134 A1 | 11/2006 | Schwammenthal et al. |
| 2006/0271166 A1 | 11/2006 | Thill et al. |
| 2006/0287668 A1 | 12/2006 | Fawzi et al. |
| 2006/0287717 A1 | 12/2006 | Rowe et al. |
| 2007/0010876 A1 | 1/2007 | Salahieh et al. |
| 2007/0010877 A1 | 1/2007 | Salahieh et al. |
| 2007/0016286 A1 | 1/2007 | Herrmann et al. |
| 2007/0055340 A1 | 3/2007 | Pryor |
| 2007/0061008 A1 | 3/2007 | Salahieh et al. |
| 2007/0112355 A1 | 5/2007 | Salahieh et al. |
| 2007/0118214 A1 | 5/2007 | Salahieh et al. |
| 2007/0162107 A1 | 7/2007 | Haug et al. |
| 2007/0173918 A1 | 7/2007 | Dreher et al. |
| 2007/0203503 A1 | 8/2007 | Salahieh et al. |
| 2007/0244552 A1 | 10/2007 | Salahieh et al. |

(56) References Cited

U.S. PATENT DOCUMENTS

| | | |
|---|---|---|
| 2007/0244555 A1 | 10/2007 | Rafiee et al. |
| 2007/0288089 A1 | 12/2007 | Gurskis et al. |
| 2008/0009940 A1 | 1/2008 | Cribier |
| 2008/0033541 A1 | 2/2008 | Gelbart et al. |
| 2008/0082165 A1 | 4/2008 | Wilson et al. |
| 2008/0109059 A1 | 5/2008 | Gordon et al. |
| 2008/0114435 A1 | 5/2008 | Bowe |
| 2008/0125859 A1 | 5/2008 | Salahieh et al. |
| 2008/0154244 A1 | 6/2008 | Singh |
| 2008/0188928 A1 | 8/2008 | Salahieh et al. |
| 2008/0208328 A1 | 8/2008 | Antocci et al. |
| 2008/0208332 A1 | 8/2008 | Lamphere et al. |
| 2008/0221672 A1 | 9/2008 | Lamphere et al. |
| 2008/0234814 A1 | 9/2008 | Salahieh et al. |
| 2008/0255542 A1 | 10/2008 | Nimgaard et al. |
| 2008/0255588 A1 | 10/2008 | Hinman |
| 2008/0255661 A1 | 10/2008 | Straubinger et al. |
| 2008/0269878 A1 | 10/2008 | Iobbi |
| 2008/0288054 A1 | 11/2008 | Pulnev et al. |
| 2009/0005863 A1 | 1/2009 | Goetz et al. |
| 2009/0018507 A1 | 1/2009 | Schmitz et al. |
| 2009/0030512 A1 | 1/2009 | Thielen et al. |
| 2009/0054969 A1 | 2/2009 | Salahieh et al. |
| 2009/0076598 A1 | 3/2009 | Salahieh et al. |
| 2009/0093877 A1 | 4/2009 | Keidar et al. |
| 2009/0171456 A1 | 7/2009 | Kveen et al. |
| 2009/0222076 A1 | 9/2009 | Figulla et al. |
| 2009/0254165 A1 | 10/2009 | Tabor et al. |
| 2009/0264759 A1 | 10/2009 | Byrd |
| 2009/0264997 A1 | 10/2009 | Salahieh et al. |
| 2009/0299462 A1 | 12/2009 | Fawzi et al. |
| 2009/0326566 A1 | 12/2009 | Alvarado |
| 2010/0010293 A1 | 1/2010 | Sato et al. |
| 2010/0030237 A1 | 2/2010 | Hayashi et al. |
| 2010/0030255 A1 | 2/2010 | Berra et al. |
| 2010/0049313 A1 | 2/2010 | Alon et al. |
| 2010/0094399 A1 | 4/2010 | Dorn et al. |
| 2010/0121434 A1 | 5/2010 | Paul et al. |
| 2010/0191326 A1 | 7/2010 | Alkhatib |
| 2010/0217274 A1 | 8/2010 | Lee et al. |
| 2010/0219092 A1 | 9/2010 | Salahieh et al. |
| 2010/0249915 A1 | 9/2010 | Zhang |
| 2010/0249916 A1 | 9/2010 | Zhang |
| 2010/0249917 A1 | 9/2010 | Zhang |
| 2010/0249918 A1 | 9/2010 | Zhang |
| 2010/0256725 A1 | 10/2010 | Rasmussen |
| 2010/0274340 A1 | 10/2010 | Hartley et al. |
| 2010/0280495 A1 | 11/2010 | Paul et al. |
| 2010/0286768 A1 | 11/2010 | Alkhatib |
| 2011/0015728 A1 | 1/2011 | Jimenez et al. |
| 2011/0054585 A1 | 3/2011 | Osborne |
| 2011/0087066 A1 | 4/2011 | Boutillette et al. |
| 2011/0088519 A1 | 4/2011 | Hu |
| 2011/0202128 A1 | 8/2011 | Duffy |
| 2011/0208296 A1 | 8/2011 | Duffy et al. |
| 2011/0251683 A1 | 10/2011 | Tabor |
| 2011/0257718 A1 | 10/2011 | Argentine |
| 2011/0257735 A1 | 10/2011 | Salahieh et al. |
| 2011/0264074 A1 | 10/2011 | Tegg et al. |
| 2011/0264199 A1 | 10/2011 | Tran et al. |
| 2011/0264204 A1 | 10/2011 | Khairkhahan |
| 2011/0270372 A1 | 11/2011 | Argentine |
| 2011/0282425 A1 | 11/2011 | Dwork |
| 2011/0295216 A1 | 12/2011 | Miller |
| 2011/0307049 A1 | 12/2011 | Kao |
| 2012/0016468 A1 | 1/2012 | Robin et al. |
| 2012/0022642 A1 | 1/2012 | Haug et al. |
| 2012/0029627 A1 | 2/2012 | Salahieh et al. |
| 2012/0035717 A1 | 2/2012 | Duffy et al. |
| 2012/0041547 A1 | 2/2012 | Duffy et al. |
| 2012/0041550 A1 | 2/2012 | Salahieh et al. |
| 2012/0046740 A1 | 2/2012 | Paul et al. |
| 2012/0053683 A1 | 3/2012 | Salahieh et al. |
| 2012/0078076 A1 | 3/2012 | Stewart et al. |
| 2012/0089224 A1 | 4/2012 | Haug et al. |
| 2012/0103840 A1 | 5/2012 | McCaffrey |
| 2012/0136425 A1 | 5/2012 | Orr |
| 2012/0172968 A1 | 7/2012 | Chuter et al. |
| 2012/0239142 A1 | 9/2012 | Liu et al. |
| 2012/0245606 A1 | 9/2012 | Goldberg et al. |
| 2012/0271398 A1 | 10/2012 | Essinger et al. |
| 2012/0296407 A1 | 11/2012 | Caselnova |
| 2012/0305441 A1 | 12/2012 | Murray et al. |
| 2012/0310332 A1 | 12/2012 | Murray et al. |
| 2012/0330409 A1 | 12/2012 | Haug et al. |
| 2013/0018457 A1 | 1/2013 | Gregg et al. |
| 2013/0030520 A1 | 1/2013 | Lee et al. |
| 2013/0123757 A1* | 5/2013 | Crisostomo ............ A61B 17/00 606/1 |
| 2013/0123796 A1 | 5/2013 | Sutton et al. |
| 2013/0123898 A1 | 5/2013 | Tung et al. |
| 2013/0123912 A1 | 5/2013 | Tung et al. |
| 2013/0131774 A1 | 5/2013 | Nabulsi et al. |
| 2013/0144276 A1 | 6/2013 | Crisostomo et al. |
| 2013/0158653 A1 | 6/2013 | Gamarra et al. |
| 2013/0158655 A1 | 6/2013 | Sutton et al. |
| 2013/0158656 A1 | 6/2013 | Sutton et al. |
| 2013/0190865 A1 | 7/2013 | Anderson |
| 2013/0304199 A1 | 11/2013 | Sutton et al. |
| 2014/0018911 A1 | 1/2014 | Zhou et al. |
| 2014/0046428 A1 | 2/2014 | Cragg et al. |
| 2014/0094904 A1 | 4/2014 | Salahieh et al. |
| 2014/0114405 A1 | 4/2014 | Paul et al. |
| 2014/0114406 A1 | 4/2014 | Salahieh et al. |
| 2014/0121766 A1 | 5/2014 | Salahieh et al. |
| 2014/0135912 A1 | 5/2014 | Salahieh et al. |
| 2014/0243967 A1 | 8/2014 | Salahieh et al. |

FOREIGN PATENT DOCUMENTS

| | | |
|---|---|---|
| DE | 19546692 A1 | 6/1997 |
| DE | 19857887 A1 | 7/2000 |
| DE | 19907646 A1 | 8/2000 |
| DE | 10049812 A1 | 4/2002 |
| DE | 10049813 C1 | 4/2002 |
| DE | 10049814 A1 | 4/2002 |
| DE | 10049815 A1 | 4/2002 |
| EP | 0103546 B1 | 5/1988 |
| EP | 0144167 B1 | 11/1989 |
| EP | 0512725 A1 | 11/1992 |
| EP | 0409929 B1 | 4/1997 |
| EP | 0850607 A1 | 7/1998 |
| EP | 0597967 B1 | 12/1999 |
| EP | 1000590 A1 | 5/2000 |
| EP | 1057459 A1 | 12/2000 |
| EP | 1057460 A1 | 12/2000 |
| EP | 1088529 A2 | 4/2001 |
| EP | 0937439 B1 | 9/2003 |
| EP | 1340473 A2 | 9/2003 |
| EP | 1356793 A2 | 10/2003 |
| EP | 1042045 B1 | 5/2004 |
| EP | 0819013 B1 | 6/2004 |
| EP | 1430853 A2 | 6/2004 |
| EP | 1435879 A1 | 7/2004 |
| EP | 1439800 A2 | 7/2004 |
| EP | 1472996 A1 | 11/2004 |
| EP | 1229864 B1 | 4/2005 |
| EP | 1430853 A3 | 6/2005 |
| EP | 1059894 B1 | 7/2005 |
| EP | 1551274 A2 | 7/2005 |
| EP | 1551336 A1 | 7/2005 |
| EP | 1078610 B1 | 8/2005 |
| EP | 1562515 A1 | 8/2005 |
| EP | 1570809 A1 | 9/2005 |
| EP | 1576937 A2 | 9/2005 |
| EP | 1582178 A2 | 10/2005 |
| EP | 1582179 A2 | 10/2005 |
| EP | 1469797 B1 | 11/2005 |
| EP | 1589902 A1 | 11/2005 |
| EP | 1600121 A1 | 11/2005 |
| EP | 1156757 B1 | 12/2005 |
| EP | 1616531 A2 | 1/2006 |
| EP | 1605871 B1 | 7/2008 |
| FR | 2788217 A1 | 7/2000 |

(56) References Cited

FOREIGN PATENT DOCUMENTS

| | | |
|---|---|---|
| GB | 2056023 A | 3/1981 |
| GB | 2398245 A | 8/2004 |
| SU | 1271508 A1 | 11/1986 |
| SU | 1371700 A1 | 2/1988 |
| WO | 9117720 A1 | 11/1991 |
| WO | 9217118 A1 | 10/1992 |
| WO | 9301768 A1 | 2/1993 |
| WO | 9315693 A1 | 8/1993 |
| WO | 9504556 A2 | 2/1995 |
| WO | 9529640 A1 | 11/1995 |
| WO | 9614032 A1 | 5/1996 |
| WO | 9624306 A1 | 8/1996 |
| WO | 9640012 A1 | 12/1996 |
| WO | 9829057 A1 | 7/1998 |
| WO | 9836790 A1 | 8/1998 |
| WO | 9850103 A1 | 11/1998 |
| WO | 9857599 A2 | 12/1998 |
| WO | 9905975 A1 | 2/1999 |
| WO | 9933414 A1 | 7/1999 |
| WO | 9940964 A1 | 8/1999 |
| WO | 9944542 A2 | 9/1999 |
| WO | 9947075 A1 | 9/1999 |
| WO | 0009059 A2 | 2/2000 |
| WO | 0041652 A1 | 7/2000 |
| WO | 0044308 A2 | 8/2000 |
| WO | 0044311 A2 | 8/2000 |
| WO | 0044313 A1 | 8/2000 |
| WO | 0045874 A1 | 8/2000 |
| WO | 0047139 A1 | 8/2000 |
| WO | 0049970 A1 | 8/2000 |
| WO | 0067661 A2 | 11/2000 |
| WO | 0105331 A1 | 1/2001 |
| WO | 0010320 A1 | 2/2001 |
| WO | 0108596 A1 | 2/2001 |
| WO | 0110343 A1 | 2/2001 |
| WO | 0135870 A1 | 5/2001 |
| WO | 0149213 A2 | 7/2001 |
| WO | 0154625 A1 | 8/2001 |
| WO | 0162189 A1 | 8/2001 |
| WO | 0164137 A1 | 9/2001 |
| WO | 0176510 A2 | 10/2001 |
| WO | 0197715 A1 | 12/2001 |
| WO | 0236048 A1 | 5/2002 |
| WO | 0239910 A2 | 5/2002 |
| WO | 0241789 A2 | 5/2002 |
| WO | 0243620 A1 | 6/2002 |
| WO | 0247575 A2 | 6/2002 |
| WO | 02056955 A1 | 7/2002 |
| WO | 02100297 A2 | 12/2002 |
| WO | 03003943 A2 | 1/2003 |
| WO | 03003949 A2 | 1/2003 |
| WO | 03011195 A2 | 2/2003 |
| WO | 03030776 A2 | 4/2003 |
| WO | 03047648 A2 | 6/2003 |
| WO | 03015851 B1 | 11/2003 |
| WO | 03094793 A1 | 11/2003 |
| WO | 03094797 A1 | 11/2003 |
| WO | 2004006803 A1 | 1/2004 |
| WO | 2004006804 A1 | 1/2004 |
| WO | 2004014256 A1 | 2/2004 |
| WO | 2004019811 A2 | 3/2004 |
| WO | 2004019817 A1 | 3/2004 |
| WO | 2004019825 A1 | 3/2004 |
| WO | 2004021922 A2 | 3/2004 |
| WO | 2004023980 A2 | 3/2004 |
| WO | 2004026117 A2 | 4/2004 |
| WO | 2004041126 A1 | 5/2004 |
| WO | 2004043293 A2 | 5/2004 |
| WO | 2004047681 A1 | 6/2004 |
| WO | 2004058106 A2 | 7/2004 |
| WO | 2004066876 A1 | 8/2004 |
| WO | 2004082536 A1 | 9/2004 |
| WO | 2004089250 A1 | 10/2004 |
| WO | 2004089253 A1 | 10/2004 |
| WO | 2004093728 A2 | 11/2004 |
| WO | 2004105651 A1 | 12/2004 |
| WO | 2005002466 A2 | 1/2005 |
| WO | 2005004753 A1 | 1/2005 |
| WO | 2005009285 A2 | 2/2005 |
| WO | 2005011534 A1 | 2/2005 |
| WO | 2005011535 A2 | 2/2005 |
| WO | 2005023155 A1 | 3/2005 |
| WO | 2005027790 A1 | 3/2005 |
| WO | 2005046528 A1 | 5/2005 |
| WO | 2005046529 A1 | 5/2005 |
| WO | 2005048883 A1 | 6/2005 |
| WO | 2005062980 A2 | 7/2005 |
| WO | 2005065585 A1 | 7/2005 |
| WO | 2005084595 A1 | 9/2005 |
| WO | 2005087140 A1 | 9/2005 |
| WO | 2005096993 A1 | 10/2005 |
| WO | 2006005015 A2 | 1/2006 |
| WO | 2006009690 A1 | 1/2006 |
| WO | 2006027499 A2 | 3/2006 |
| WO | 2006138391 A2 | 12/2006 |
| WO | 2007033093 A2 | 3/2007 |
| WO | 2007035471 A2 | 3/2007 |
| WO | 2007044285 A2 | 4/2007 |
| WO | 2007053243 A2 | 4/2007 |
| WO | 2007058847 A2 | 5/2007 |
| WO | 2007092354 A2 | 8/2007 |
| WO | 2007097983 A2 | 8/2007 |
| WO | 2010022138 A2 | 2/2010 |
| WO | 2010042950 A2 | 4/2010 |
| WO | 2011137531 A1 | 11/2011 |
| WO | 2012155130 A1 | 11/2012 |

OTHER PUBLICATIONS

US 8,211,170, 7/2012, Paul et al. (withdrawn)
Invitation to Pay Additional Fees and, where applicable, Protest Fee, PCT/US2016/049693, dated Nov. 9, 2016.
Laborde et al., "Percutaneous Implantation of the Corevalve Aortic Valve Prosthesis for Patients Presenting High Risk for Surgical Valve Replacement." EuroIntervention: 472-474, Feb. 2006.
Supplemental Search Report from EP Patent Office, EP Application No. 04813777.2, Aug. 19, 2011.
"A Matter of Size." Triennial Review of the National Nanotechnology Initiative, The National Academies Press, Washington DC, v-13, http://www.nap.edu/catalog/11752/a-matter-of-size-triennial-review-of-the-national-nanotechnology, 2006.
"Heart Valve Materials—Bovine (cow)." Equine & Porcine Pericardium, Maverick Biosciences Pty. Lt, http://maverickbio.com/biological-medical-device-materials.php?htm. 2009.
"Pericardial Heart Valves." Edwards Lifesciences, Cardiovascular Surgery FAQ, http://www.edwards.com/products/cardiovascularsurgeryfaq.htm, Nov. 14, 2010.
Andersen et al., "Transluminal implantation of artificial heart valves. Description of a new expandable aortic valve and initial results with implantation by catheter technique in closed chest pigs." Euro. Heart J., 13:704-708, May 1992.
Atwood et al., "Insertion of Heart Valves by Catheterization." Project Supervised by Prof. S. Muftu of Northeastern University 2001-2002: 36-40, May 30, 2002.
Atwood et al., "Insertion of Heart Valves by Catheterization." The Capstone Design Course Report. MIME 1501-1502. Technical Design Report. Northeastern University, pp. 1-93, Nov. 5, 2007.
Bodnar et al., "Replacement Cardiac Valves R Chapter 13: Extinct Cardiac Valve Prostheses." Pergamon Publishing Corporation. New York, 307-322, 1991.
Boudjemline et al., "Percutaneous Implantation of a Biological Valve in the Aorta to Treat Aortic Valve Insufficiency—A Sheep Study." Med Sci. Monit., vol. 8, No. 4: BR113-116, Apr. 12, 2002.
Boudjemline et al., "Percutaneous Implantation of a Valve in the Descending Aorta in Lambs." Euro. Heart J., 23: 1045-1049, Jul. 2002.
Boudjemline et al., "Percutaneous Pulmonary Valve Replacement in a Large Right Ventricular Outflow Tract: An Experimental Study." Journal of the American College of Cardiology, vol. 43(6): 1082-1087, Mar. 17, 2004.

(56) References Cited

OTHER PUBLICATIONS

Boudjemline et al., "Percutaneous Valve Insertion: A New Approach?" J. of Thoracic and Cardio. Surg, 125(3): 741-743, Mar. 2003.
Boudjemline et al., "Steps Toward Percutaneous Aortic Valve Replacement." Circulation, 105: 775-778, Feb. 12, 2002.
Cribier et al., "Early Experience with Percutaneous Transcatheter Implantation of Heart Valve Prosthesis for the Treatment of End-Stage Inoperable Patients with Calcific Aortic Stenosis." J. of Am. Coll. of Cardio, 43(4): 698-703, Feb. 18, 2004.
Cribier et al., "Percutaneous Transcatheter Implantation of an Aortic Valve Prosthesis for Calcific Aortic Stenosis: First Human Case." Percutaneous Valve Technologies, Inc., 16 pages, Apr. 16, 2002.
Cribier et al., "Percutaneous Transcatheter Implementation of an Aortic Valve Prosthesis for Calcific Aortic Stenosis: First Human Case Description." Circulation, 106: 3006-3008, Dec. 10, 2002.
Cunanan et al., "Tissue Characterization and Calcification Potential of Commercial Bioprosthetic Heart Valves." Ann. Thorac. Surg., S417-421, May 15, 2001.
Cunliffe et al., "Glutaraldehyde Inactivation of Exotic Animal Viruses in Swine Heart Tissue." Applied and Environmental Microbiology, Greenport, New York, 37(5): 1044-1046, May 1979.
EP Search Report for EP Application No. 06824992.9, dated Aug. 10, 2011.
Examiner's First Report on AU Patent Application No. 2011202667, dated May 17, 2012.
Ferrari et al., "Percutaneous Transvascular Aortic Valve Replacement with Self-Expanding Stent-Valve Device." Poster from the presentation given at SMIT 2000, 12th International Conference. Sep. 5, 2000.
Helmus, "Mechanical and Bioprosthetic Heart Valves in Biomaterials for Artificial Organs." Woodhead Publishing Limited: 114-162, 2011.
Hijazi, "Transcatheter Valve Replacement: A New Era of Percutaneous Cardiac Intervention Begins." J. of Am. College of Cardio., 43(6): 1088-1089, Mar. 17, 2004.
Hourihan et al., "Transcatheter Umbrella Closure of Valvular and Paravalvular Leaks." JACC, Boston, Massachusetts, 20(6): 1371-1377, Nov. 15, 1992.
Huber et al., "Do Valved Stents Compromise Coronary Flow?" European Journal of Cardio-thoracic Surgery, vol. 25: 754-759, Jan. 23, 2004.
Knudsen et al., "Catheter-implanted prosthetic heart valves." Int'l J. of Art. Organs, 16(5): 253-262, May 1993.
Kort et al., "Minimally Invasive Aortic Valve Replacement: Echocardiographic and Clinical Results." Am. Heart J., 142(3): 476-481, Sep. 2001.
Levy, "*Mycobacterium chelonei* Infection of Porcine Heart Valves." The New England Journal of Medicine, Washington DC, 297(12), Sep. 22, 1977.
Love et al., The Autogenous Tissue Heart Valve: Current Status. Journal of Cardiac Surgery, 6(4): 499-507, Mar. 1991.
Lutter et al., "Percutaneous Aortic Valve Replacement: An Experimental Study. I. Studies on Implantation." J. of Thoracic and Cardio. Surg., 123(4): 768-776, Apr. 2002.
Moulopoulos et al., "Catheter-Mounted Aortic Valves." Annals of Thoracic Surg., 11(5): 423-430, May 1971.
Paniagua et al., "Heart Watch." Texas Heart Institute. Edition: 8 pages, Spring, 2004.
Paniagua et al., "Percutaneous Heart Valve in the Chronic in Vitro Testing Model." Circulation, 106: e51-e52, Sep. 17, 2002.
Pavcnik et al., "Percutaneous Bioprosthetic Venous Valve: A Long-term Study in Sheep." J. of Vascular Surg., 35(3): 598-603, Mar. 2002.
Phillips et al., "A Temporary Catheter-Tip Aortic Valve: Hemodynamic Effects on Experimental Acute Aortic Insufficiency." Annals of Thoracic Surg., 21(2): 134-136, Feb. 1976.
Sochman et al., "Percutaneous Transcatheter Aortic Disc Valve Prosthesis Implantation: A Feasibility Study." Cardiovasc. Intervent. Radiol., 23: 384-388, Sep. 2000.
Southern Lights Biomaterials Homepage, http://www.slv.co.nz/, Jan. 7, 2011.
Stassano. "Mid-term Results of the Valve-on-Valve Technique for Bioprosthetic Failure." European Journal of Cardiothoracic Surgery: vol. 18, 453-457, Oct. 2000.
Stuart, "In Heart Valves, a Brave, New Non-Surgical World." Start-Up. 9-17, Feb. 2004.
Supplemental Search Report from EP Patent Office, EP Application No. 04815634.3, Aug. 19, 2011.
Supplemental Search Report from EP Patent Office, EP Application No. 05758878.2, Oct. 24, 2011.
Topol. "Percutaneous Expandable Prosthetic Valves." Textbook of Interventional Cardiology, W.B. Saunders Company, 2: 1268-1276, 1994.
Vahanian et al., "Percutaneous Approaches to Valvular Disease." Circulation, 109: 1572-1579, Apr. 6, 2004.
Van Herwerden et al., "Percutaneous Valve Implantation: Back to the Future?" Euro. Heart J., 23(18): 1415-1416, Sep. 2002.
Zhou et al, "Self-expandable Valved Stent of Large Size: Off-Bypass Implantation in Pulmonary Position." Eur. J. Cardiothorac, 24: 212-216, Aug. 2003.

\* cited by examiner

MEDICAL DEVICE HANDLE

RELATED APPLICATIONS

This application claims priority to U.S. Provisional Application No. 62/335,999, filed May 13, 2016.

TECHNICAL FIELD

The present disclosure pertains to medical devices, and methods for manufacturing and/or using medical devices. More particularly, the present disclosure pertains to configurations of a replacement heart valve.

BACKGROUND

A wide variety of intracorporeal medical devices have been developed for medical use, for example, intravascular use. Some of these devices include guidewires, catheters, medical device delivery systems (e.g., for stents, grafts, replacement valves, etc.), and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

SUMMARY

In a first aspect, a medical device handle for percutaneous delivery of a medical implant from a tubular member extending distally from the medical device handle, may comprise a handle housing having a longitudinal axis extending from a proximal end of the handle housing to a distal end of the handle housing, the handle housing including a cavity disposed within the handle housing, and a carriage assembly disposed within the cavity and operatively connected to the tubular member and the medical implant, the carriage assembly being longitudinally movable between a distal position and a proximal position by rotation of a control knob with respect to the handle housing, the control knob being disposed around the proximal end of the handle housing. The carriage assembly may include a carriage member, a first sliding member, a second sliding member, and a locking element configured to releasably fix the first sliding member and the second sliding member relative to the carriage member. The locking element may be rotatable relative to the handle housing.

In addition or alternatively, and in a second aspect, a medical device handle may further include a tubular collar member disposed around a proximal portion of the handle housing, the tubular collar member being rotatable about the handle housing.

In addition or alternatively, and in a third aspect, the locking element physically engages the carriage member.

In addition or alternatively, and in a fourth aspect, rotating the tubular collar member about the longitudinal axis rotates the locking element out of engagement with the carriage member.

In addition or alternatively, and in a fifth aspect, after rotating the locking element out of engagement with the carriage member, the first sliding member is longitudinally movable with respect to the second sliding member.

In addition or alternatively, and in a sixth aspect, the first sliding member is movable proximally, from a first position to a second position, relative to the second sliding member.

In addition or alternatively, and in a seventh aspect, in the second position, the first sliding member abuts a portion of the second sliding member.

In addition or alternatively, and in an eighth aspect, after rotating the locking element out of engagement with the carriage member, further rotation of the tubular collar member moves the first sliding member proximally relative to the second sliding member.

In addition or alternatively, and in a ninth aspect, after the first sliding member is in the second position, further rotation of the tubular collar member moves the second sliding member proximally relative to the carriage member.

In addition or alternatively, and in a tenth aspect, after the first sliding member is in the second position, further rotation of the tubular collar member moves both the first sliding member and the second sliding member proximally relative to the carriage member.

In addition or alternatively, and in an eleventh aspect, the second sliding member includes at least one actuator member extending distally therefrom to the medical implant, wherein movement of the carriage assembly from the distal position toward the proximal position places the at least one actuator member in tension.

In addition or alternatively, and in a twelfth aspect, after releasing the first sliding member and the second sliding member from the carriage member, releases tension on the at least one actuator member until the first sliding member re-engages the second sliding member at a proximal end of a slot formed in the second sliding member.

In addition or alternatively, and in a thirteenth aspect, a medical device handle for percutaneous delivery of a medical implant from a tubular member extending distally from the medical device handle may comprise a handle housing having a longitudinal axis extending from a proximal end of the handle housing to a distal end of the handle housing, the handle housing including a cavity disposed within the handle housing, a carriage assembly disposed within the cavity and operatively connected to the tubular member and the medical implant, the carriage assembly being longitudinally movable between a distal position and a proximal position by rotation of a control knob with respect to the handle housing, the control knob being disposed around the proximal end of the handle housing, wherein the carriage assembly includes a carriage member, a first sliding member, a second sliding member, and a locking element configured to releasably fix the first sliding member and the second sliding member relative to the carriage member, the locking element being rotatable relative to the handle housing, and a tubular collar member disposed around a proximal portion of the handle housing, the tubular collar member being rotatable about the handle housing. The handle housing may include a button mechanism configured to engage the tubular collar member in a first orientation of the tubular collar member relative to the handle housing when the first sliding member and the second sliding member are fixed to the carriage member by the locking element, and the button mechanism is configured to engage the tubular collar member in a second orientation of the tubular collar member relative to the handle housing when the first sliding member and the second sliding member are not fixed to the carriage member by the locking element.

In addition or alternatively, and in a fourteenth aspect, at least a portion of the button mechanism extends radially outward from the handle housing.

In addition or alternatively, and in a fifteenth aspect, when the button mechanism is engaged with the tubular collar member in the first orientation of the tubular collar member, the tubular collar member is prevented from rotating about the handle housing.

In addition or alternatively, and in a sixteenth aspect, when the button mechanism is engaged with the tubular collar member in the second orientation of the tubular collar member, the tubular collar member is prevented from rotating about the handle housing.

In addition or alternatively, and in a seventeenth aspect, a medical device system may comprise a handle housing including a longitudinally movable carriage assembly disposed therein, the carriage assembly including a carriage member, a first slider member, a second slider member, and a locking element releasably fixing the first slider member and the second slider member relative to the carriage member, the locking element being rotatable with respect to the handle housing, a tubular member extending distally from the handle housing, a replacement heart valve deployable from a distal end of the tubular member, at least one actuator member extending distally from the carriage assembly through the tubular member to the replacement heart valve, the at least one actuator member being releasably attached to the replacement heart valve, and a tubular collar member disposed around and rotatable with respect to the handle housing, the tubular collar member being configured to release the first sliding member and the second sliding member from the carriage member upon rotation about the handle housing.

In addition or alternatively, and in an eighteenth aspect, partial rotation of the tubular collar member about the handle housing translates the first sliding member proximally relative to the second sliding member until the first sliding member abuts a portion of the second sliding member, thereby irreversibly detaching the at least one actuator member from the replacement heart valve.

In addition or alternatively, and in a nineteenth aspect, partial rotation of the tubular collar member about the handle housing after the first sliding member abuts the portion of the second sliding member translates the second sliding member proximally relative to the carriage member.

In addition or alternatively, and in a twentieth aspect, translation of the second sliding member proximally relative to the carriage member proximally retracts the at least one actuator member from the replacement heart valve.

The above summary of some embodiments, aspects, and/or examples is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description of various embodiments in connection with the accompanying drawings, in which.

Figure 1:
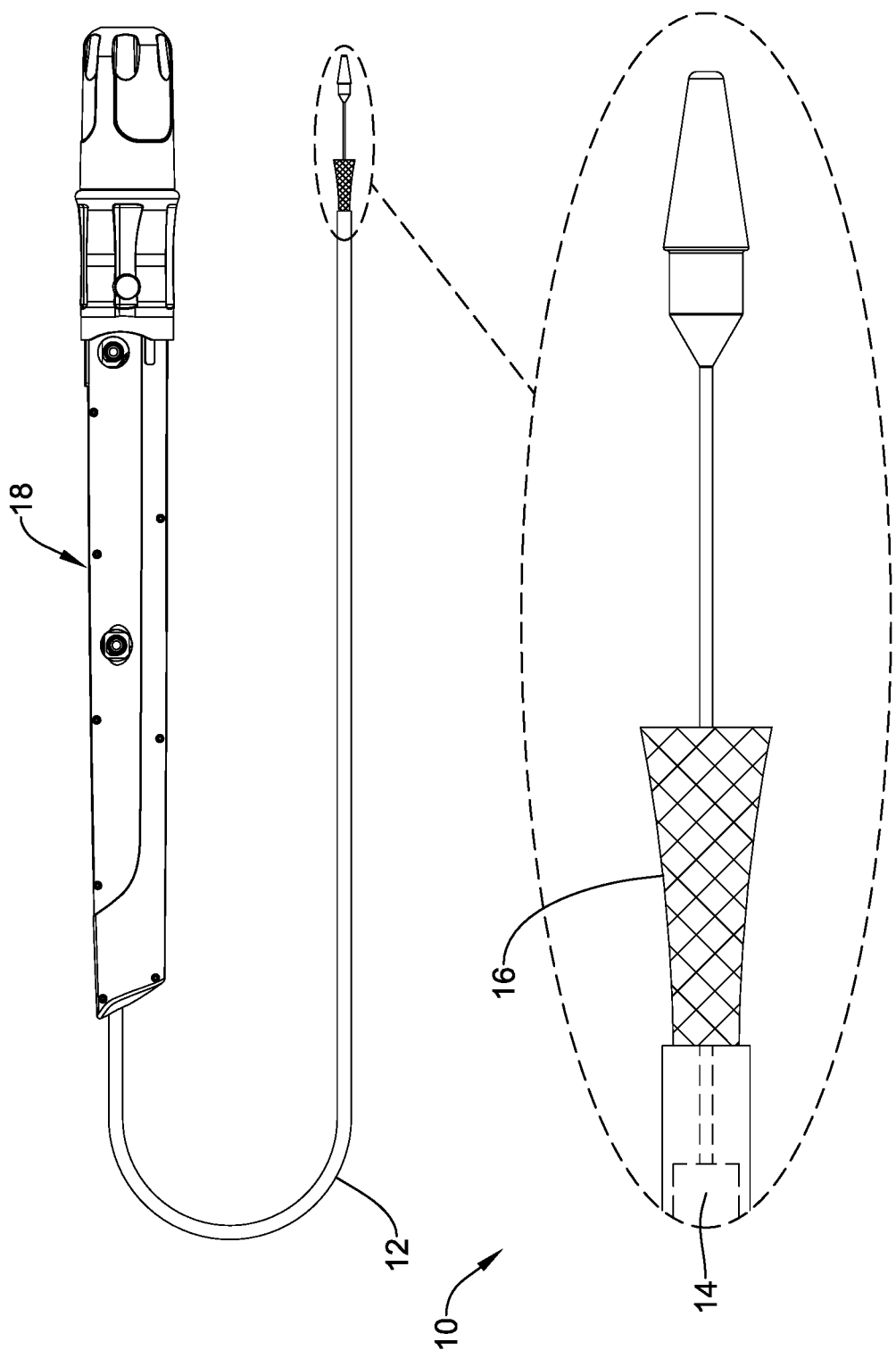
FIG. 1 illustrates an example medical device system.

While aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

The following description should be read with reference to the drawings, which are not necessarily to scale, wherein like reference numerals indicate like elements throughout the several views. The detailed description and drawings are intended to illustrate but not limit the claimed invention. Those skilled in the art will recognize that the various elements described and/or shown may be arranged in various combinations and configurations without departing from the scope of the disclosure. The detailed description and drawings illustrate example embodiments of the claimed invention.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (e.g., having the same function or result). In many instances, the term "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g., 1 to 5 includes 1, 1.5, 2, 2.75, 3, 3.80, 4, and 5).

Although some suitable dimensions, ranges, and/or values pertaining to various components, features and/or specifications are disclosed, one of skill in the art, incited by the present disclosure, would understand desired dimensions, ranges, and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

Relative terms such as "proximal", "distal", "advance", "retract", variants thereof, and the like, may be generally be considered with respect to the positioning, direction, and/or operation of various elements relative to a user/operator/manipulator of the device, wherein "proximal" and "retract" indicate or refer to closer to or toward the user and "distal" and "advance" indicate or refer to farther from or away from the user. Other relative terms, such as "upstream", "downstream", "inflow", and "outflow" refer to a direction of fluid flow within a lumen, such as a body lumen, a blood vessel, or within a device.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect such feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously-used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

Diseases and/or medical conditions that impact the cardiovascular system are prevalent throughout the world. Traditionally, treatment of the cardiovascular system was often conducted by directly accessing the impacted part of the system. For example, treatment of a blockage in one or more of the coronary arteries was traditionally treated using coronary artery bypass surgery. As can be readily appreciated, such therapies are rather invasive to the patient and require significant recovery times and/or treatments. More recently, less invasive therapies have been developed, for example, where a blocked coronary artery could be accessed and treated via a percutaneous catheter (e.g., angioplasty). Such therapies have gained wide acceptance among patients and clinicians.

Some relatively common medical conditions may include or be the result of inefficiency, ineffectiveness, or complete failure of one or more of the valves within the heart. For example, failure of the aortic valve or the mitral valve can have a serious effect on a human and could lead to serious health condition and/or death if not dealt with properly. Treatment of defective heart valves poses other challenges in that the treatment often requires the repair or outright replacement of the defective valve. Such therapies may be highly invasive to the patient. Disclosed herein are medical devices that may be used for delivering a medical device to a portion of the cardiovascular system in order to diagnose, treat, and/or repair the system. At least some of the medical devices disclosed herein may be used to deliver and implant a replacement heart valve (e.g., a replacement aortic valve, replacement mitral valve, etc.). In addition, the devices disclosed herein may deliver the replacement heart valve percutaneously and, thus, may be much less invasive to the patient. The devices disclosed herein may also provide a number of additional desirable features and benefits as described in more detail below.

The figures illustrate selected components and/or arrangements of a medical device system 10, shown schematically in FIG. 1 for example. It should be noted that in any given figure, some features of the medical device system 10 may not be shown, or may be shown schematically, for simplicity. Additional details regarding some of the components of the medical device system 10 may be illustrated in other figures in greater detail. A medical device system 10 may be used to deliver and/or deploy a variety of medical devices to a number of locations within the anatomy. In at least some embodiments, the medical device system 10 may include a replacement heart valve delivery system (e.g., a replacement aortic valve delivery system) that can be used for percutaneous delivery of a medical implant 16, such as a replacement heart valve. This, however, is not intended to be limiting as the medical device system 10 may also be used for other interventions including valve repair, valvuloplasty, and the like, or other similar interventions.

The medical device system 10 may generally be described as a catheter system that includes an outer sheath 12, an inner catheter 14 (a portion of which is shown in FIG. 1 in phantom line) extending at least partially through a lumen of the outer sheath 12, and a medical implant 16 (e.g., a replacement heart valve implant, for example, which term may be used interchangeably with the term "medical implant" herein) which may be coupled to the inner catheter 14 and disposed within a lumen of the outer sheath 12 during delivery of the medical implant 16. In some embodiments, a medical device handle 18 may be disposed at a proximal end of the outer sheath 12 and/or the inner catheter 14 and may include one or more actuation means associated therewith. In other words, a tubular member (e.g., the outer sheath 12, the inner catheter 14, etc.) may extend distally from the medical device handle 18. In general, the medical device handle 18 may be configured to manipulate the position of the outer sheath 12 relative to the inner catheter 14 and/or aid in the deployment of the medical implant 16. In some embodiments, the medical device system 10 may include a nose cone disposed at a distal end of a guidewire extension tube, wherein the guidewire extension tube may extend distally from the inner catheter 14 and/or the outer sheath 12. In at least some embodiments, the nose cone may be designed to have an atraumatic shape and/or may include a ridge or ledge that it configured to abut a distal end of the outer sheath 12 during delivery of the medical implant 16.

Figure 2:
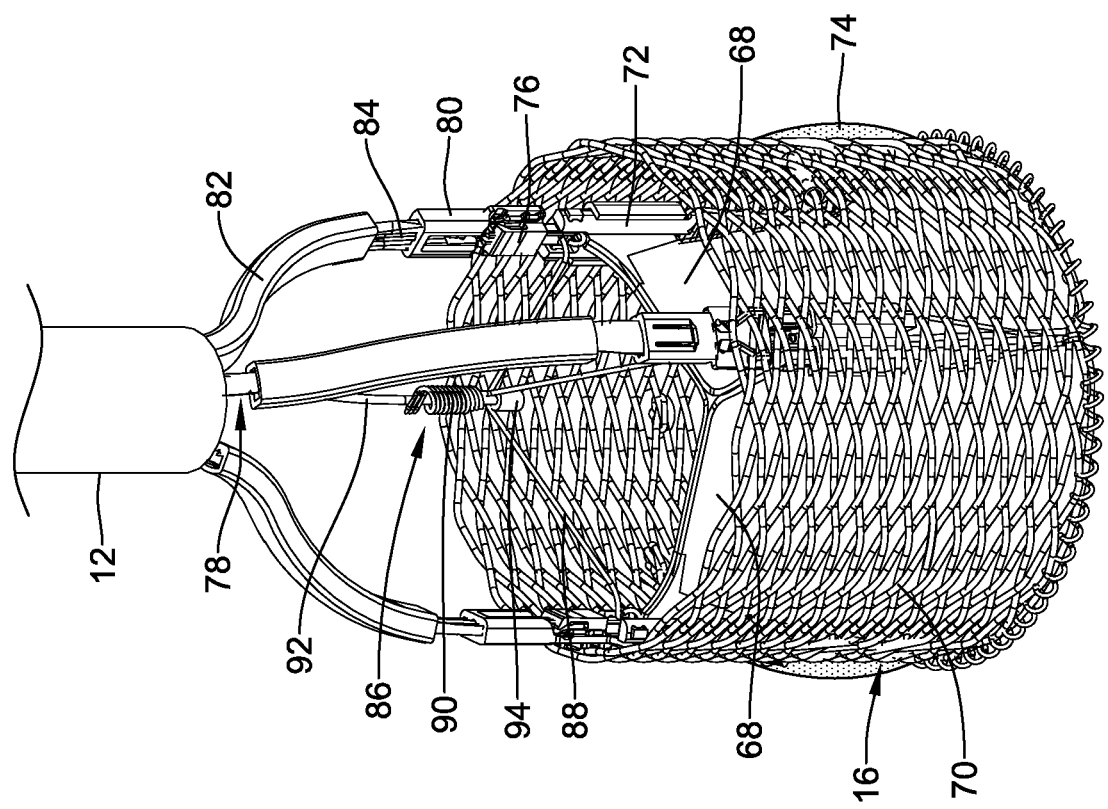
FIG. 2 illustrates selected components of an example medical implant associated with the medical device system.
Figure 3:
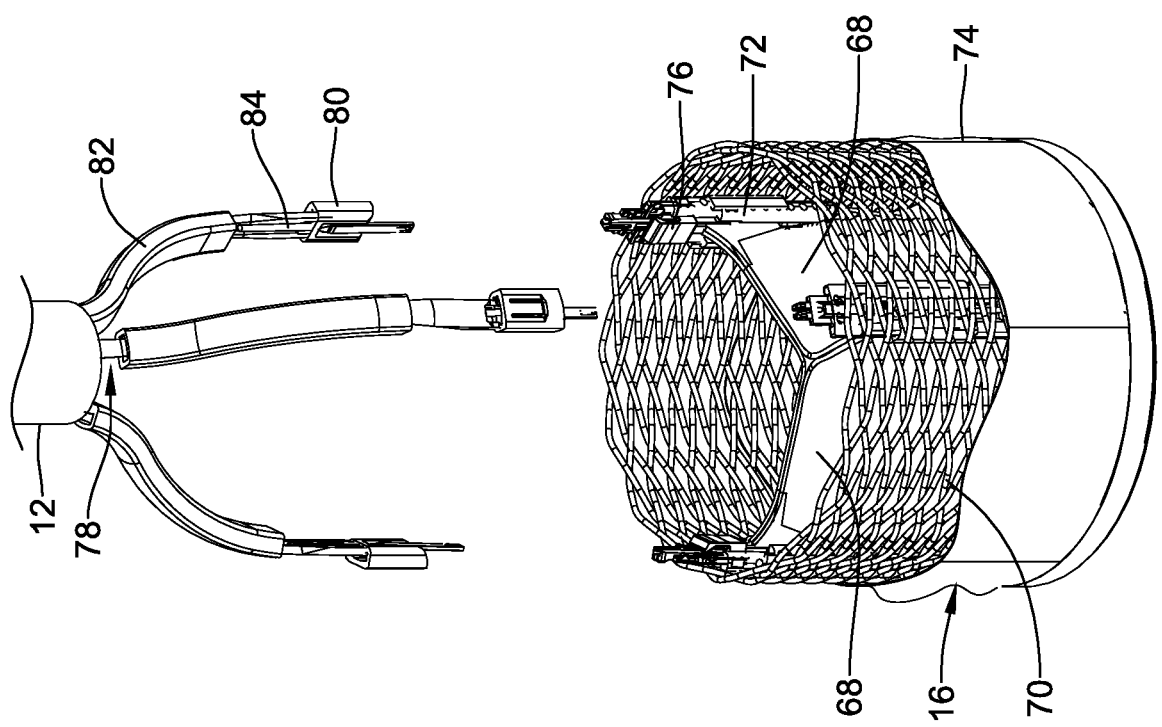
FIG. 3 illustrates selected components of an example medical implant associated with the medical device system.

In use, the medical device system 10 may be advanced percutaneously through the vasculature to a position adjacent to an area of interest and/or a treatment location. For example, in some embodiments, the medical device system 10 may be advanced through the vasculature to a position adjacent to a defective native valve (e.g., aortic valve, mitral valve, etc.). Alternative approaches to treat a defective aortic valve and/or other heart valve(s) are also contemplated with the medical device system 10. During delivery, the medical implant 16 may be generally disposed in an elongated and low profile "delivery" configuration within the lumen and/or a distal end of the outer sheath 12, as seen schematically in FIG. 1 for example. Once positioned, the outer sheath 12 may be retracted relative to the medical implant 16 and/or the inner catheter 14 to expose the medical implant 16. In some embodiments, the medical implant 16 may be disposed in an "everted" configuration while disposed within the lumen and/or the distal end of the outer sheath 12 and/or immediately upon exposure after retracting the outer sheath 12. In some embodiments, the "delivery" configuration and the "everted" configuration may be substantially similar and/or may be used interchangeably. The medical implant 16 may be actuated using the medical device handle 18 in order to translate the medical implant 16 into a generally shortened and larger profile "deployed" configuration suitable for implantation within the anatomy, as seen in FIG. 2 for example. When the medical implant 16 is suitably deployed within the anatomy, the medical device system 10 may be disconnected, detached, and/or released from the medical implant 16 and the medical device system 10 can be removed from the vasculature, leaving the medical implant 16 in place in a "released" configuration, as seen in FIG. 3, to function as, for example, a suitable replacement for the native valve. In at least some interventions, the medical implant 16 may be deployed within the native valve (e.g., the native valve is left in place and not excised). Alternatively, the native valve may be removed and the medical implant 16 may be deployed in its place as a replacement.

In some embodiments, the outer sheath 12 and/or the inner catheter 14 may take the form of an extruded polymer tube. Other forms are also contemplated including other polymer tubes, metallic tubes, reinforced tubes, or the like including other suitable materials such as those disclosed herein. In some embodiments, the outer sheath 12 and/or the inner catheter 14 may be a singular monolithic or unitary member. In other embodiments, the outer sheath 12 and/or the inner catheter 14 may include a plurality of portions or segments that are coupled together. In some embodiments, the outer sheath 12 and/or the inner catheter 14 may also be curved, for example adjacent to the distal end thereof. In some embodiments, the outer sheath 12 and/or the inner catheter 14 may have one or more sections with a differing hardness/stiffness (e.g., differing shore durometer).

In some embodiments, the inner catheter 14 may include one or more lumens extending longitudinally through the inner catheter 14. For example, the inner catheter 14 may include a first lumen, a second lumen, a third lumen, and a fourth lumen. In general, the lumens may extend along an entire length of the inner catheter 14. Other embodiments are contemplated, however, where one or more of the lumens extend along only a portion of the length of the inner catheter 14.

In some embodiments, disposed within the first lumen may be at least one actuator member 84, which may be used to reversibly actuate (e.g., translate axially or longitudinally and/or expand radially) the medical implant 16 between the "delivery" configuration and the "deployed" configuration, as explained in more detail herein. For the purposes of this disclosure and any related proceedings, the terms "actuator member" and "push-pull rod" (including both singular and plural forms thereof) may be used interchangeably herein. In some embodiments, the medical device system 10 may include at least one actuator member 84 extending from a medical device handle 18 to a medical implant 16. In some embodiments, the at least one actuator member 84 may include a plurality of actuator members 84, two actuator members 84, three actuator members 84, four actuator members 84, or another suitable or desired number of actuator members 84. For the purpose of illustration only, the medical device system 10 and/or the medical implant 16 is shown with three actuator members 84.

In some embodiments, disposed within the second lumen may be a pin release mandrel 92 and/or at least one release pin 88, although dedicated release pins 88 are not strictly necessary. In some embodiments, the third lumen may be a guidewire lumen configured to slidably receive a guidewire therein. In some embodiments, the fourth lumen may be used to house a non-stretch wire or other reinforcing member. The exact form of the non-stretch wire or other reinforcing member may vary. In some embodiments, the non-stretch wire or other reinforcing member may be embedded within the fourth lumen and/or the inner catheter 14. In addition, the non-stretch wire or other reinforcing member may extend to a position adjacent to the distal end but not fully to the distal end of the inner catheter 14. For example, in some embodiments, a short distal segment of the fourth lumen may be filled in with polymer material adjacent to the distal end of the inner catheter 14.

FIGS. 2 and 3 illustrate selected components of the medical device system 10 and/or the medical implant 16 in the "deployed" configuration (as seen in FIG. 2) and the "released" configuration (as seen in FIG. 3). For example, here it can be seen that the medical implant 16 includes a plurality of valve leaflets 68 (e.g., bovine pericardial, polymeric, etc.) which may be secured to a tubular anchor member 70 that is reversibly actuatable between the "delivery" configuration, as in FIG. 1 for example, and the "deployed" configuration. In some embodiments, the tubular anchor member 70 may include a proximal end and a distal end. In some embodiments, the tubular anchor member 70 may be substantially cylindrical in shape or configuration. In some embodiments, the tubular anchor member 70 may define a central longitudinal axis extending from the proximal end of the tubular anchor member 70 to the distal end of the tubular anchor member 70, and/or a lumen extending through the tubular anchor member 70 along, parallel to, coaxial with, and/or coincident with the central longitudinal axis. In some embodiments, the tubular anchor member 70 may be and/or include a braid formed from one or more filaments or wires (e.g., a single filament or wire, two filaments, or wires, etc.). Other shapes and/or configurations are also contemplated. Some suitable but non-limiting materials for the tubular anchor member 70, for example metallic materials or polymeric materials, may be described below.

In some embodiments, the tubular anchor member 70 may include and/or form a plurality of anchor member intersection points distributed around a circumference of the tubular anchor member 70. In some embodiments, the plurality of anchor member intersection points may include two or more overlapping segments (e.g., a first segment, a second segment, a third segment, etc.) of the tubular anchor member 70 and/or the braid, filaments, wires, etc. thereof. In some embodiments, the two or more overlapping segments may be arranged in an alternating over-and-under pattern or arrangement. For example, at a first anchor member intersection point, a first segment may be disposed radially outward of a second segment. At an adjacent second anchor member intersection point including the first segment, the first segment may be disposed radially inward of an overlapping segment (e.g., a third segment). If the first segment (or any single segment) is followed around the circumference of the tubular anchor member 70, the over-under-over pattern would continue alternating about the entire circumference of the tubular anchor member 70.

In some embodiments, the medical implant 16 may include a plurality of locking mechanisms attached to the tubular anchor member 70, the plurality of locking mechanisms being configured to secure the tubular anchor member 70 in the "deployed" configuration and/or the "released" configuration. In some embodiments, the at least one actuator member 84 may be configured to engage with the plurality of locking mechanisms and actuate the tubular anchor member 70 and/or the medical implant 16 between the "delivery" configuration, the "deployed" configuration, and/or the "released" configuration. In some embodiments, one actuator member 84 may correspond to, engage with, and/or actuate one locking mechanism. In some embodiments, one actuator member 84 may correspond to, engage with, and/or actuate more than one locking mechanism. Other configurations are also contemplated.

In some embodiments, the plurality of locking mechanisms may each comprise an axially movable post member 72, for example at the commissure portions of the valve leaflets 68 (the post member 72 may sometimes be referred to as a "commissure post", which may serve to secure the plurality of valve leaflets 68), and a buckle member 76 fixedly attached to the tubular anchor member 70 (e.g., along an interior surface of the tubular anchor member 70). In some embodiments, each of the plurality of valve leaflets 68 may be secured to the tubular anchor member 70 at one post member 72. In some embodiments, each of the plurality of valve leaflets 68 may be secured to two adjacent post members 72 at opposing sides of the valve leaflets 68. In other words, in at least some embodiments, a medical implant 16 may include a plurality of post members 72 and a corresponding plurality of buckle members 76. Other configurations and correspondences are also contemplated. In the illustrated example(s), the medical implant 16 includes three valve leaflets 68 secured to the tubular anchor member 70 with three post members 72. The plurality of valve leaflets 68 may also be secured to the base or "distal end" of the tubular anchor member 70. The plurality of post members 72, in turn, may be secured to the tubular anchor member 70 (e.g., along an interior surface of the tubular anchor member 70) with sutures or other suitable means.

In some embodiments, the at least one actuator member 84 may be configured to engage with the plurality of locking mechanisms and actuate the tubular anchor member 70 and/or the medical implant 16 between the "delivery" configuration, the "deployed" configuration, and/or the "released" configuration. In some embodiments, one actuator member 84 may correspond to, engage with, and/or actuate one locking mechanism. In some embodiments, the actuator member 84 may be generally round, oblong, ovoid, rectangular, polygonal (e.g., two-sided, three-sided, four-sided, five-sided, six-sided, etc.) in shape. Other shapes, both regular and irregular, are also contemplated. In some embodiments, the actuator member 84 may be formed from a single piece of wire, round stock, or other suitable material, as discussed herein. In some embodiments, the actuator member 84 may be formed by further processing the single piece of wire, round stock, or other suitable material, such as by machining, stamping, laser cutting, or other suitable techniques. Some suitable but non-limiting materials for the actuator member 84, for example metallic materials or polymeric materials, may be described below.

It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For example, a reference to "the actuator member", "the locking element", "the lumen", or other features may be equally referred to all instances and quantities beyond one of said feature. For simplicity and clarity purposes, not all elements of the disclosed invention are necessarily shown in each figure or discussed in detail below. In some illustrative examples, only one of the plurality of actuator members 84, only one of the plurality of the post members 72, only one of the plurality of the buckle members 76, etc., are shown and discussed (and/or the whole medical implant 16 and/or the tubular anchor member 70 may not be shown to facilitate understanding of certain elements). However, it will be understood that the following discussion may apply equally to any and/or all of the components for which there are more than one within the medical implant 16 (e.g., the at least one actuator member 84, the plurality of locking elements, etc.) and/or the medical device system 10, unless explicitly stated to the contrary. Additionally, not all instances of some elements or features may be shown in each figure for clarity.

In some embodiments, the post member 72 may engage the buckle member 76 in the "deployed" configuration, and consequently, in the "released" configuration. In some embodiments, the post member 72 may be axially and/or longitudinally spaced apart from the buckle member 76 in the "delivery" configuration and/or the "everted" configuration. Some suitable but non-limiting materials for the post member 72 and/or the buckle member 76, for example metallic materials or polymeric materials, may be described below.

In some embodiments, a distal end of the post member 72 may be secured and/or attached (e.g., fixedly attached, movably attached, removably attached, etc.) to a distal portion of the tubular anchor member 70, such as by a suture, a tether, adhesives, or other suitable element. In some embodiments, the post member 72 may be movable relative to the tubular anchor member 70 and/or the buckle member 76. In some embodiments, the post member 72 may be axially or longitudinally movable relative to the tubular anchor member 70 and/or the buckle member 76. In some embodiments, the buckle member 76 may be fixedly attached to the tubular anchor member 70. Other embodiments are contemplated where the buckle member 76 may be movably or removably attached to the tubular anchor member 70. In some embodiments, the post member 72 may be secured or attached (e.g., fixedly attached, movably attached, removably attached, etc.) to a distal end of the tubular anchor member 70. In some embodiments, the buckle member 76 may be fixed or attached to a proximal portion of the tubular anchor member 70. In some embodiments, the buckle member 76 may be fixed or attached at or to a proximal end of the tubular anchor member 70.

In some embodiments, the medical implant 16 may include one or more of the plurality of valve leaflets 68 secured to the tubular anchor member 70 at, adjacent to, and/or using (at least in part) the plurality of post members 72. In some embodiments, the plurality of valve leaflets 68 may also be secured to a base, or the distal end, of the tubular anchor member 70. As such, when the post member 72 is pulled proximally to engage the buckle member 76, as will be described herein, the distal end of the tubular anchor member 70 may also be pulled proximally relative to the buckle member 76, thereby transitioning the tubular anchor member 70 and/or the medical implant 16 from the "delivery" configuration and/or the "everted" configuration toward the "deployed" configuration.

In at least some embodiments, the distal end of the tubular anchor member 70 may be interchangeably described as the "inflow" end or the "upstream" end of the tubular anchor member 70 and/or the medical implant 16. In at least some embodiments, the proximal end of the tubular anchor member 70 may be interchangeably described as the "outflow" end or the "downstream" end of the tubular anchor member 70 and/or the medical implant 16.

In some embodiments, the plurality of valve leaflets 68 may be coupled and/or secured (e.g., to the post member 72, to the tubular anchor member 70, and/or back to themselves) using one or more sutures, threads, wires, filaments, or other suitable elements. In some embodiments, the plurality of valve leaflets 68 may be coupled and/or secured (e.g., to the post member 72, to the tubular anchor member 70, and/or back to themselves) using an adhesive, a bonding agent, or other suitable securing means. In some embodiments, the plurality of valve leaflets 68 may be coupled and/or secured (e.g., to the post member 72, to the tubular anchor member 70, and/or back to themselves) using a fabric, a textile, or other thin flexible material.

In some embodiments, the tubular anchor member 70 may have a total of three buckle members 76 and three post members 72 attached and/or secured thereto. Similarly, one actuator member 84 may be operatively associated with each post member 72 and buckle member 76, for a total of three actuator members 84 in the illustrated example(s). Other embodiments are contemplated where fewer or more buckle members 76, post members 72, actuator members 84, etc. may be utilized.

In some embodiments, a seal member 74 may be circumferentially disposed on and/or about a distal portion and/or an inflow portion of the tubular anchor member 70, as seen in FIGS. 2 and 3 for example, and as the term suggests, may help to seal an exterior of the medical implant 16 and/or the tubular anchor member 70 within and/or against a target site or area of interest upon deployment (e.g., in the "deployed" configuration and/or the "released" configuration), thereby preventing leakage around the medical implant 16 and/or the tubular anchor member 70. In some embodiments, the seal member 74 may be disposed about and/or radially outward of an outside surface of the tubular anchor member 70. In some embodiments, the seal member 74 may be disposed around a perimeter and/or on or against an exterior or outer surface of the tubular anchor member 70. In some embodiments, the seal member 74 may be coupled and/or secured at the distal end and/or the inflow end of the tubular anchor member 70.

In some embodiments, the seal member 74 may include a plurality of layers of polymeric material. Some suitable polymeric materials may include, but are not necessarily limited to, polycarbonate, polyurethane, polyamide, polyether block amide, polyethylene, polyethylene terephthalate, polypropylene, polyvinylchloride, polytetrafluoroethylene, polysulfone, and copolymers, blends, mixtures or combinations thereof. Other configurations and/or other suitable materials are also contemplated.

In some embodiments, a distal end of the seal member 74 may include a reinforcing band fixedly attached to the seal member 74 at and/or adjacent the distal end and/or the inflow end of the tubular anchor member 70. In some embodiments, the reinforcing band may be integrally formed with, incorporated into, adhered to, and/or at least partially embedded within the seal member 74. In some embodiments, the reinforcing band may be formed from a woven or nonwoven fabric strip, a textile, or other thin flexible material. The reinforcing band may provide tear resistance in the vicinity of sutures, filaments, or other attachment elements associated with components or aspects of the medical implant 16. In some embodiments, the seal member 74 and/or the reinforcing band may extend longitudinally beyond the distal end and/or the inflow end of the tubular anchor member 70.

In some embodiments, attachment between the medical implant 16 and the inner catheter 14 (and/or the outer sheath 12) may be effected through the use of a coupler 78. The coupler 78 may generally include a cylindrical base (not shown) that may be disposed about, attached to, and/or extending from a distal end of the inner catheter 14 (and/or the outer sheath 12). Projecting distally from the base is a plurality of fingers (e.g., two fingers, three fingers, four fingers, etc.) that are each configured to engage with the medical implant 16 at one of the plurality of the buckle members 76 (for example, at a proximal end of the buckle members 76), with the plurality of actuator members 84 extending therethrough and engaging the post members 72. A collar 80 may be disposed about each of the fingers of the coupler 78 to further assist in holding together the fingers and the buckle members 76. A guide 82 may be disposed over each of the fingers proximal of the collar 80 and may serve to keep the fingers of the coupler 78 associated with the actuator members 84 extending adjacent to (and axially slidable relative to) the fingers of the coupler 78. Finally, in some embodiments, a pin release assembly 86, as shown in FIG. 2 for example, may be a linking structure that keeps the post members 72, the buckle members 76, and the actuator members 84 associated with one another. The pin release assembly 86 may include a plurality of release pins 88 that may be joined together (e.g. via a coiled connection 90) and held to a pin release mandrel 92 (with a ferrule 94, for example). As mentioned above, the pin release assembly 86 may not be present in all embodiments of the medical implant 16, and in at least some embodiments, may utilize one or more of various "pinless" release and/or locking mechanisms. Other suitable configurations are also contemplated. Some suitable but non-limiting materials for the coupler 78, the fingers, the collars 80, the guides 82, and/or the pin release assembly 86, for example metallic materials or polymeric materials, may be described below.

During delivery, the medical implant 16 may be secured at the distal end of the inner catheter 14 by virtue of the association of the fingers of the coupler 78 being coupled with a projecting proximal end of the buckle members 76 (and being held in place with the collar 80 disposed over the connection) and by virtue of the actuator members 84 and the post members 72 being operatively secured together. When the medical implant 16 is advanced within the anatomy to the desired location, the outer sheath 12 may be withdrawn (e.g., moved proximally relative to the inner catheter 14 and/or the medical implant 16) to expose the medical implant 16. Then, the actuator members 84 can be used to translate and "lock" the tubular anchor member 70 and/or the medical implant 16 in the "deployed" configuration by proximally retracting the actuator members 84 to pull the post members 72 into engagement with the buckle members 76. Finally, in some embodiments, the release pins 88 can be removed, thereby uncoupling the actuator members 84 from the post members 72, which allows the tubular anchor member 70 and/or the medical implant 16 to be released from the medical device system 10 and left in the anatomy in the "released" configuration. In some embodiments, the release pins 88 and/or the pin release assembly 86 may not be present, and other and/or alternative means of releasing the medical implant 16 may be utilized, such as a displacement-based or distance-based means of releasing the medical implant 16.

Figure 4:
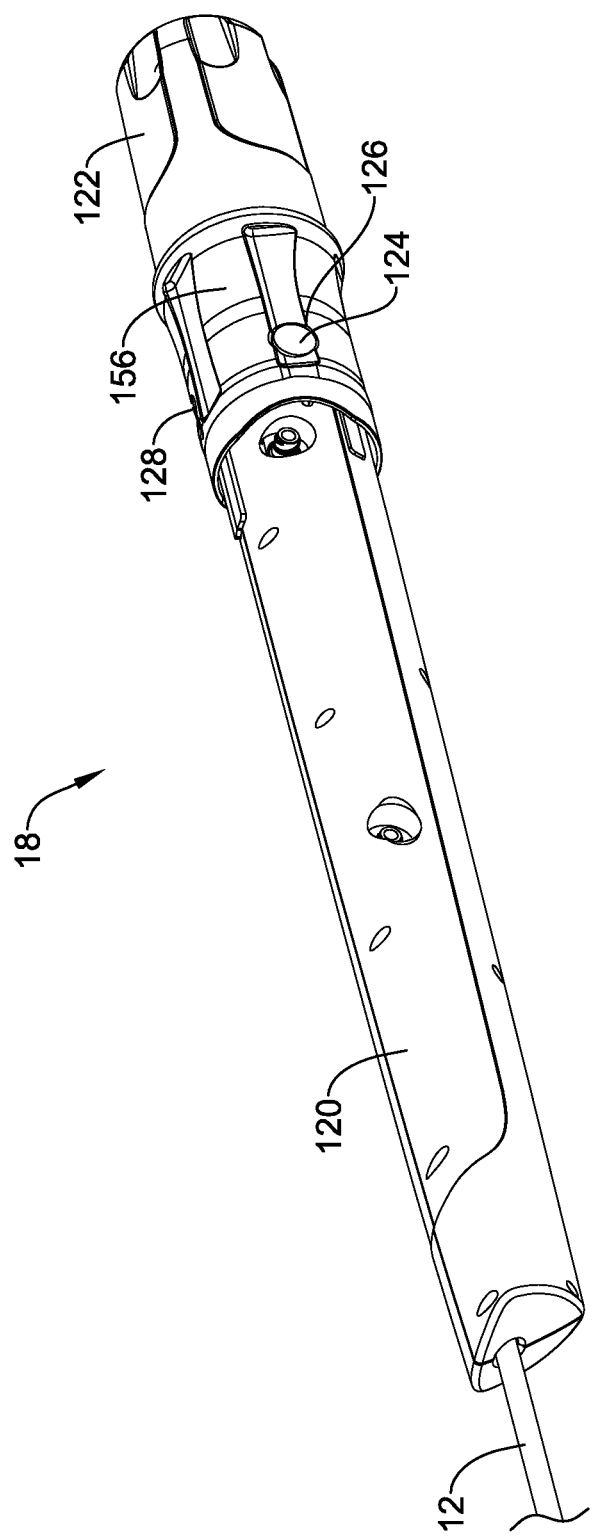
FIG. 4 illustrates an example medical device handle.
Figure 5:
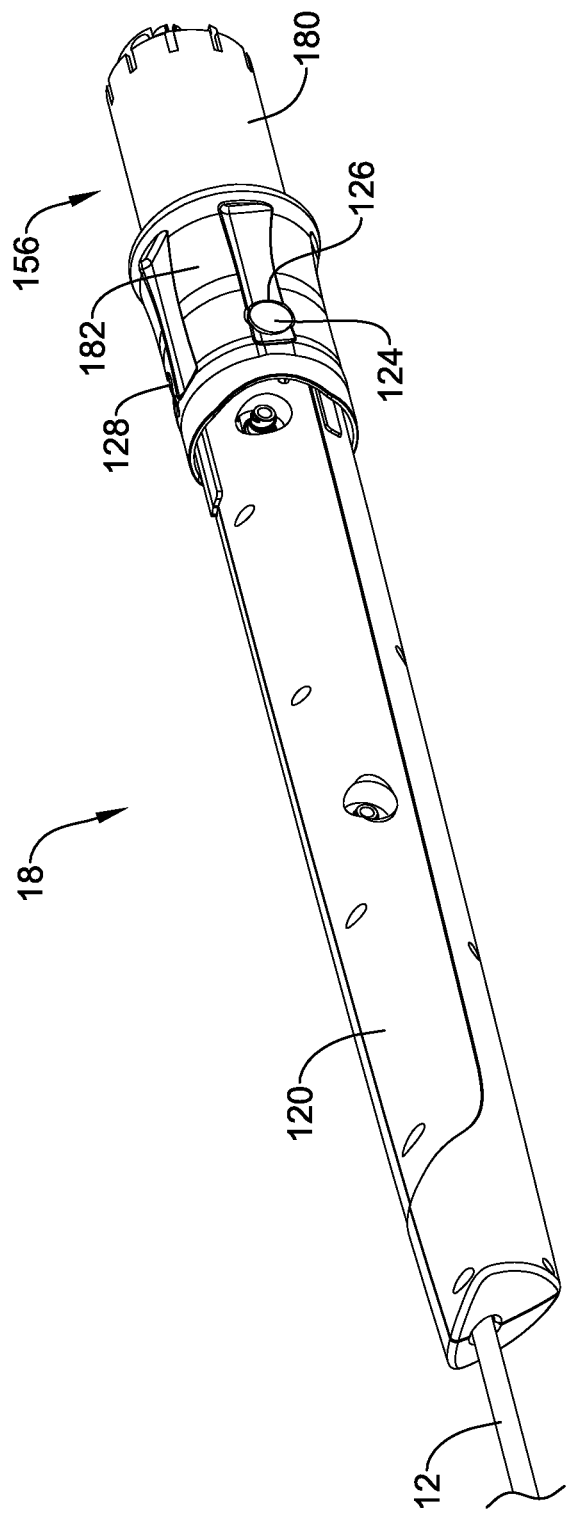
FIG. 5 illustrates selected components of an example medical device handle.
Figure 6:
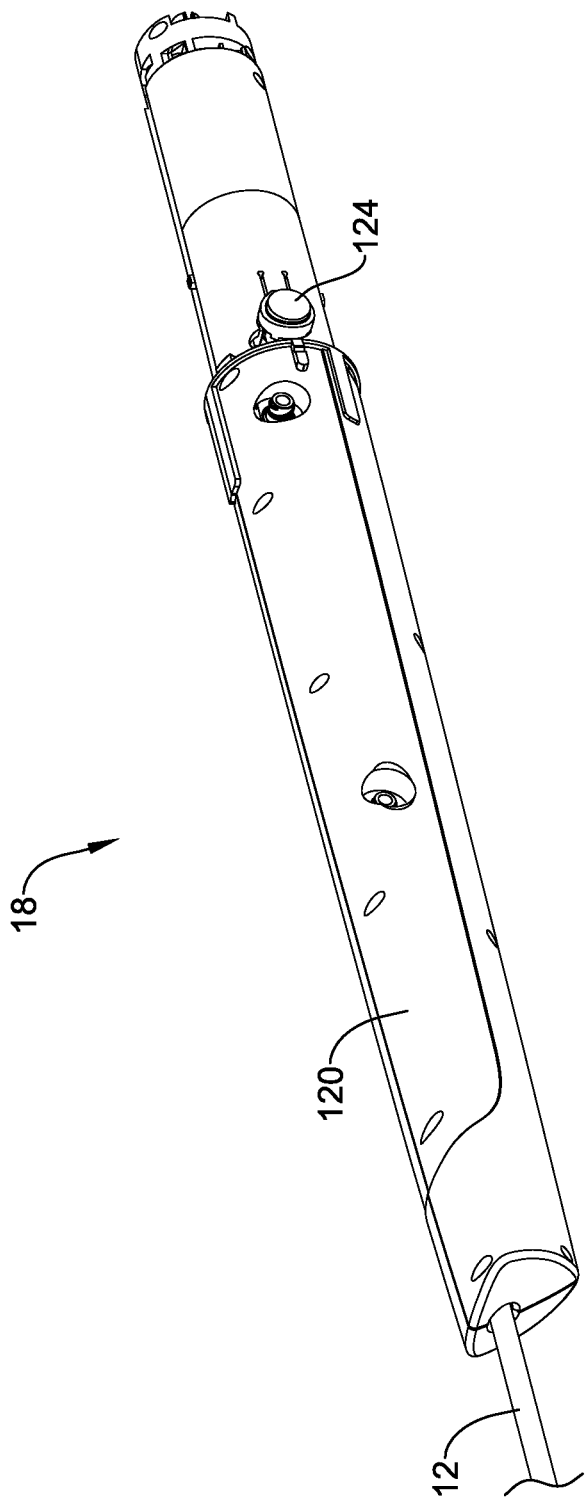
FIG. 6 illustrates selected components of an example medical device handle.

FIGS. 4-6 illustrate an example medical device handle 18. Here it can be seen that the medical device handle 18 may include an elongated handle housing 120. The handle housing 120 may define a longitudinal axis extending from a proximal end of the handle housing 120 to a distal end of the handle housing 120. In some embodiments, the handle housing 120 may include a cavity disposed within the handle housing 120. A rotatable control knob 122 may be disposed about the handle housing 120 (e.g., at a proximal end of the handle housing 120) and may be used to actuate and/or move one or more of the components of the medical device system 10 (e.g., the outer sheath 12, the actuator members 84, etc.). In some embodiments, the rotatable control knob 122 may be rotatable about and/or with respect to the handle housing 120.

In some embodiments, the handle housing 120 may include an axial translation mechanism disposed therein and operatively connected to the rotatable control knob 122. In some embodiments, the axial translation mechanism may include a carriage assembly (described further below) disposed within the cavity and/or the handle housing 120. In some embodiments, the carriage assembly disposed within the cavity and/or the handle housing 120 may be operatively connected to the tubular member extending distally from the medical device handle 18 (e.g., the outer sheath 12, the inner catheter 14, etc.) and/or to the medical implant 16. In some embodiments, the carriage assembly 145 may be longitudinally movable within the cavity and/or the handle housing 120 between a distal position and a proximal position by rotation of the rotatable control knob 122 with respect to the handle housing 120. In some embodiments, the axial translation mechanism may convert rotational motion of the rotatable control knob 122 into axial translation of the carriage assembly disposed within the cavity and/or the handle housing 120, as will become apparent from the discussion below.

In some embodiments, a tubular collar member 156 may be disposed about a proximal portion of the handle housing 120. In some embodiments, the tubular collar member 156 may be rotatable about and/or with respect to the handle housing 120. In some embodiments, such as shown in FIG. 5, the rotatable control knob 122 may be disposed about a proximal portion 180 of the tubular collar member 156. In some embodiments, the rotatable control knob 122 may be rotatable about and/or with respect to the tubular collar member 156. In some embodiments, the medical device handle 18 may also include one or more apertures through the elongated handle housing 120 and/or flush ports accessible therethrough that can be used to flush certain elements (e.g., components, lumens, etc.) of the medical device system 10 as described herein.

In some embodiments, the medical device handle 18 and/or the handle housing 120 may include a button mechanism 124 configured to engage with and/or extend into a first aperture 126 extending through a wall of the tubular collar member 156 in a first orientation of the tubular collar member 156 relative to the handle housing 120. In some embodiments, the button mechanism 124 may be configured to engage with and/or extend into a second aperture 128 extending through the wall of the tubular collar member 156 in a second orientation of the tubular collar member 156 relative to the handle housing 120. In some embodiments, the second orientation may be different from the first orientation. In some embodiments, at least a portion of the button mechanism 124 extends radially outward from the handle housing 120 relative to the longitudinal axis of the handle housing 120.

In some embodiments, the button mechanism 124 may be actuatable between a first position and a second position relative to the tubular collar member 156, the handle housing 120, and/or the longitudinal axis of the handle housing 120 to release an interlock feature and permit the tubular collar member 156 to rotate about and/or relative to the elongated handle housing 120 to place the medical device system 10 in condition to translate and/or actuate the medical implant 16 from the "deployed" configuration to the "released" configuration. In some embodiments, the second position may be disposed radially inward of the first position. In other words, in order to activate and/or actuate the button mechanism 124, the button mechanism 124 must be moved, translated, and/or pressed radially inward toward the longitudinal axis of the handle housing 120 from the first position to the second position. In some embodiments, after activating and/or actuating the button mechanism 124 to the second position, the tubular collar member 156 may be rotated about and/or relative to the elongated handle housing 120 to move one or more components of the medical device system 10 (e.g., the pin release mandrel 92, etc.).

In some embodiments, when the button mechanism 124 is engaged with the tubular collar member 156 in the first orientation of the tubular collar member 156 (for example, with the button mechanism 124 disposed in the first position), the tubular collar member 156 may be locked and/or prevented from rotating about and/or relative to the handle housing 120. In some embodiments, when the button mechanism 124 is engaged with the tubular collar member 156 in the second orientation of the tubular collar member 156 (for example, with the button mechanism 124 disposed in the first position), the tubular collar member 156 may be locked and/or prevented from rotating about and/or relative to the handle housing 120. In some embodiments, when the button mechanism 124 is disposed is the second position, the tubular collar member 156 may be released and/or permitted to rotate about and/or with respect to the handle housing 120. Other means of locking and/or releasing the tubular collar member 156 relative to the handle housing 120 are also contemplated.

Figure 7:
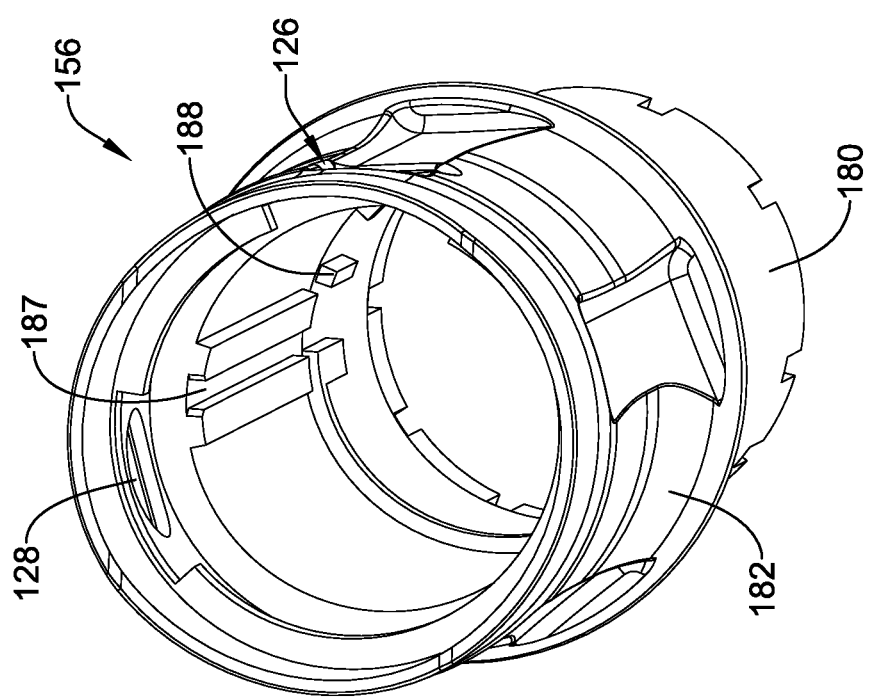
FIGS. 7-8 illustrate an example collar associated with the example medical device handle.
Figure 8:
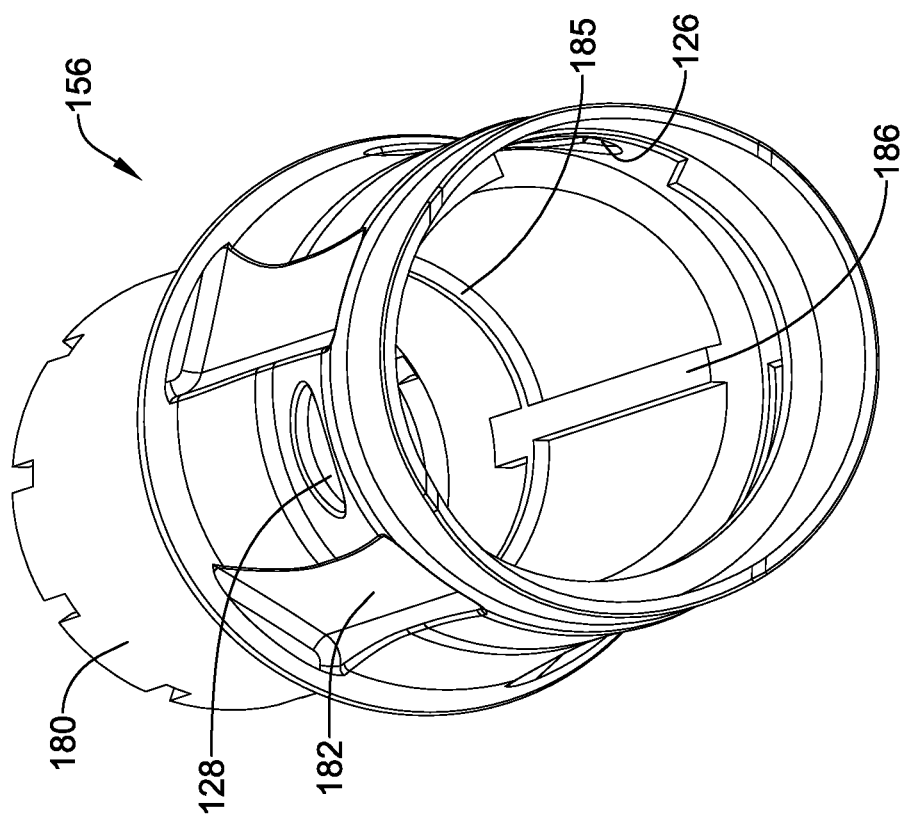

FIGS. 7 and 8 illustrate certain aspects of an example tubular collar member 156. In some embodiments, the tubular collar member 156 may include a proximal portion 180 and a distal portion 182. In some embodiments, the proximal portion 180 may include a plurality of notches at a proximal end of the tubular collar member 156, the plurality of notches being configured to engage with a rotatable ring, as discussed below. In some embodiments, the rotatable control knob 122 may be disposed about and/or over the proximal portion 180 of the tubular collar member 156. In some embodiments, the distal portion 182 may be contoured and/or include indentations to facilitate grasping by a user to rotate the tubular collar member 156 about and/or relative to handle housing 120.

In some embodiments, the distal portion 182 of the tubular collar member 156 may include a first aperture 126 and/or a second aperture 128 disposed in and/or extending through a wall of the tubular collar member 156. In some embodiments, the first aperture 126 and/or the second aperture 128 may be configured to receive at least a portion of the button mechanism 124 therein. In some embodiments, the tubular collar member 156 may include a middle portion disposed between the proximal portion 180 and the distal portion 182. In some embodiments, the middle portion may extend radially outward farther than the proximal portion 180 and/or the distal portion 182, and/or may form a radially extending ridge along an outer surface of the tubular collar member 156.

In some embodiments, the tubular collar member 156 may include one or more slots, ridges, and/or features disposed along an inner surface of the tubular collar member 156. In some embodiments, the tubular collar member 156 may include a first internally-extending longitudinal ridge 186 extending radially inward from an inner surface of the tubular collar member 156 less than a full length of the tubular collar member 156. In some embodiments, carriage assembly 145 may include a carriage member 152 configured to engage with a second sliding member 150 to actuate and/or translate the actuator members 84 relative to the handle housing 120. In at least some embodiments, the carriage member 152 may include a laterally-extending protrusion or flag member 164 (seen in FIG. 9, for example) configured to engage with and/or travel along the first internally-extending longitudinal ridge 186 until it reaches a circumferential internally-extending ridge 185. Upon reaching the circumferential internally-extending ridge 185, proximal translation of the carriage member 152 may cease and/or is prevented by interference between the circumferential internally-extending ridge 185 and the flag member 164. In general, the laterally-extending protrusion or flag member 164 may be designed as a feature that can prevent the tubular collar member 156 from being rotated earlier than desired. For example, the laterally-extending protrusion or flag member 164 may be positioned to follow the first internally-extending longitudinal ridge 186 along the inner surface of the tubular collar member 156. In at least some embodiments, the tubular collar member 156 may be prevented from rotating about the handle housing 120 by interference between the first internally-extending longitudinal ridge 186 and the flag member 164.

In some embodiments, a first internally-facing longitudinal slot 187 may guide a portion of the locking element 148 as the carriage assembly 145 and/or the locking element 148 is translated proximally within the handle housing 120. In at least some embodiments, the locking element 148 may be prevented from rotating about a lead screw 162 by interference between the first internally-facing longitudinal slot 187 and the portion of the locking element 148 extending into the first internally-facing longitudinal slot 187.

Figure 9:
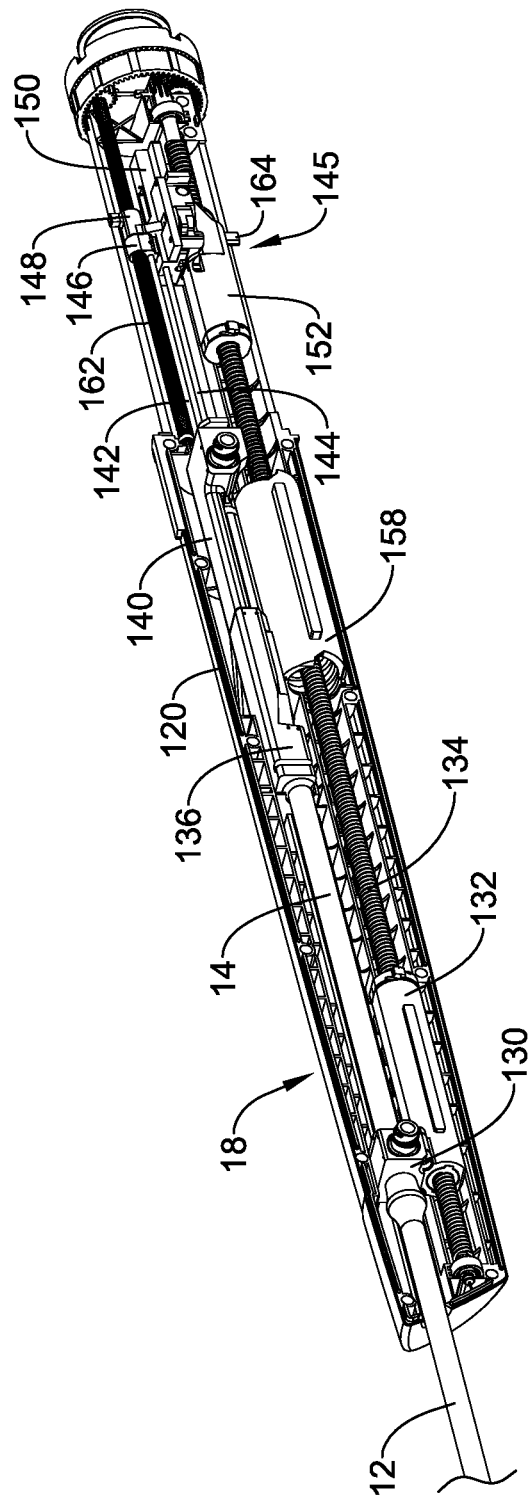
FIG. 9 is a partial cut-away view illustrating selected components associated with the example medical device handle.

FIG. 9 illustrates the medical device handle 18 with a portion of the handle housing 120 removed, exposing at least some of the components disposed within the cavity. Here it can be seen that a proximal end of the outer sheath 12 may be fixedly attached to a sheath adapter 130. The sheath adapter 130 may be fixedly attached to a sheath carriage 132, which may be threaded onto a lead screw 134. A distal flush port may be disposed on the sheath adapter 130. In general, the distal flush port may provide access to the interior or lumen of the outer sheath 12 (e.g., access to space between the inner catheter 14 and the outer sheath 12) so that a clinician can flush fluid through the lumen of the outer sheath 12 to remove any unwanted materials (e.g., air, fluid, contaminants, etc.) therein prior to use of the medical device system 10. In at least some embodiments, the distal flush port may have a luer type connector (e.g., a one-way luer connector) that allows a device such as a syringe with a corresponding connector to be attached thereto for flushing.

In some embodiments, the inner catheter 14 may extend through and proximally from the sheath adapter 130. A proximal end of the inner catheter 14 may be attached (e.g., fixedly attached) to a diverter 136. The diverter 136 may be attached to a support body 140. In general, the diverter 136 and/or the support body 140 may have one or more passageways or lumens formed therein. In some embodiments, the actuator members 84 and/or the pin release mandrel 92 may extend through respective (e.g., different) passageways or lumens formed in the diverter 136 and/or the support body 140. Alternatively, the proximal ends of the actuator members 84 and/or the pin release mandrel 92 may each be fixedly attached to a shaft (e.g., solid in cross-section, tubular, etc.), and each of the shafts may extend through the one or more passageways or lumens. For example, a first shaft 142 and a second shaft 144 may extend through the passageways in the diverter 136, and in some embodiments, the first shaft 142 extends through a first passageway and the second shaft 144 extends through a second passageway that is separate or distinct from the first passageway. In at least some embodiments, the first shaft 142 may be fixedly attached to the pin release mandrel 92. In at least some embodiments, the second shaft 144 may be fixedly attached to the actuator members 84. It should be noted that at in least some embodiments of the medical device system 10, three actuator members 84 are utilized. In these embodiments, the three actuator members 84 may come together (e.g., brought into contact with one another or otherwise brought into relatively close proximity with one another) adjacent to the distal end of the inner catheter 14. At one or more positions along their length, the actuator members 84 may be fixedly attached (e.g., welded, etc.) to one another.

In some embodiments, a hypotube may extend through the diverter 136 within a passageway therein and then be "diverted" around a portion of the diverter 136 and the support body 140, and ultimately be extended to a position at the proximal end of the medical device handle 18 so as to provide a user access to a guidewire lumen of the inner catheter 14. A proximal flush port may be disposed on the support body 140 that can be used to flush the lumens of the inner catheter 14 and, for example, may function similarly to the distal flush port.

In some embodiments, the medical device handle 18 may include a carriage assembly 145 movably disposed within the cavity. In some embodiments, the carriage assembly 145 may be longitudinally movable between a distal position and a proximal position within the cavity by rotation of the rotatable control knob 122 with respect to the handle housing 120. In some embodiments, the carriage assembly 145 may include a carriage member 152, a first sliding member 146, a second sliding member 150, and a locking element 148 configured to releasably fix the first sliding member 146 and/or the second sliding member 150 to the carriage member 152. In some embodiments, the carriage assembly 145 and/or the carriage member 152 may be threaded onto and/or axially translatable along a lead screw 134 disposed within the handle housing 120.

At their respective proximal ends, the first shaft 142 and/or the pin release mandrel 92 may be secured to the first sliding member 146, and the second shaft 144 and/or the actuator members 84 may be secured to the second sliding member 150. In other words, the second sliding member 150 may include at least one actuator member 84 (and/or the second shaft 144) extending distally therefrom to the medical implant 16. The connections between the various components may include a number of different types of connections including mechanical bonding (e.g., pinning, threading, interference fit, etc.), adhesive bonding, thermal bonding, etc. In some embodiments, the first sliding member 146 may be releasably fixed to and/or selectively slidable relative to the second sliding member 150 and/or the carriage member 152. In some embodiments, the first sliding member 146 may be releasably fixed and/or selectively locked to the second sliding member 150 and/or the carriage member 152 by the locking element 148, thereby preventing relative movement between the first sliding member 146 and the second sliding member 150. The second sliding member 150 may releasably fixed and/or selectively locked to the carriage member 152 by the locking element 148. Thus, rotation of the lead screw 134 can cause axial movement and/or translation of the carriage assembly 145, the carriage member 152, the first sliding member 146, and the second sliding member 150 along the lead screw 134 and/or with and/or relative to the handle housing 120. Thus, movement of the carriage assembly 145 from the distal position toward the proximal position may place the at least one actuator member 84 into tension, and/or the actuator members 84 may also be axially translated relative to the handle housing 120 (via second shaft 144) by rotation of the lead screw 134. Some additional details regarding this motion can be found herein.

In general, the medical device handle 18 may include and/or define a stop feature (e.g., a hard stop, interference member, etc.) that prevents the carriage assembly 145 and/or the carriage member 152 from translating further in a proximal direction, and/or may provide tactile feedback (e.g., resistance to further rotation of the rotatable control knob 122) to the user indicating that the plurality of actuator members 84 have been retracted proximally a sufficient distance to lock the post members 72 with the buckle members 76 (e.g., to actuate the medical implant 16 and/or the tubular anchor member 70 into the "deployed" configuration). To verify proper locking and/or positioning of the medical implant 16, a clinician may use an appropriate visualization technique (for example, to visualize the plurality of locking mechanisms, etc.).

The locking element 148 may be positioned adjacent to first sliding member 146 to selectively lock the first sliding member 146 to the second sliding member 150. In order to allow the pin release mandrel 92 to be proximally retracted to pull the release pins 88, the locking element 148 can be rotated or otherwise moved to a secondary position or configuration. When in this configuration, the locking element 148 no longer forms a barrier to further movement of, for example, the first sliding member 146 and the pin release mandrel 92. Accordingly, with the locking element 148 no longer acting as an impediment, the first sliding member 146 and the pin release mandrel 92 can be proximally retracted to facilitate deployment of the medical implant 16 by allowing the release pins 88 to be pulled.

Figure 15:
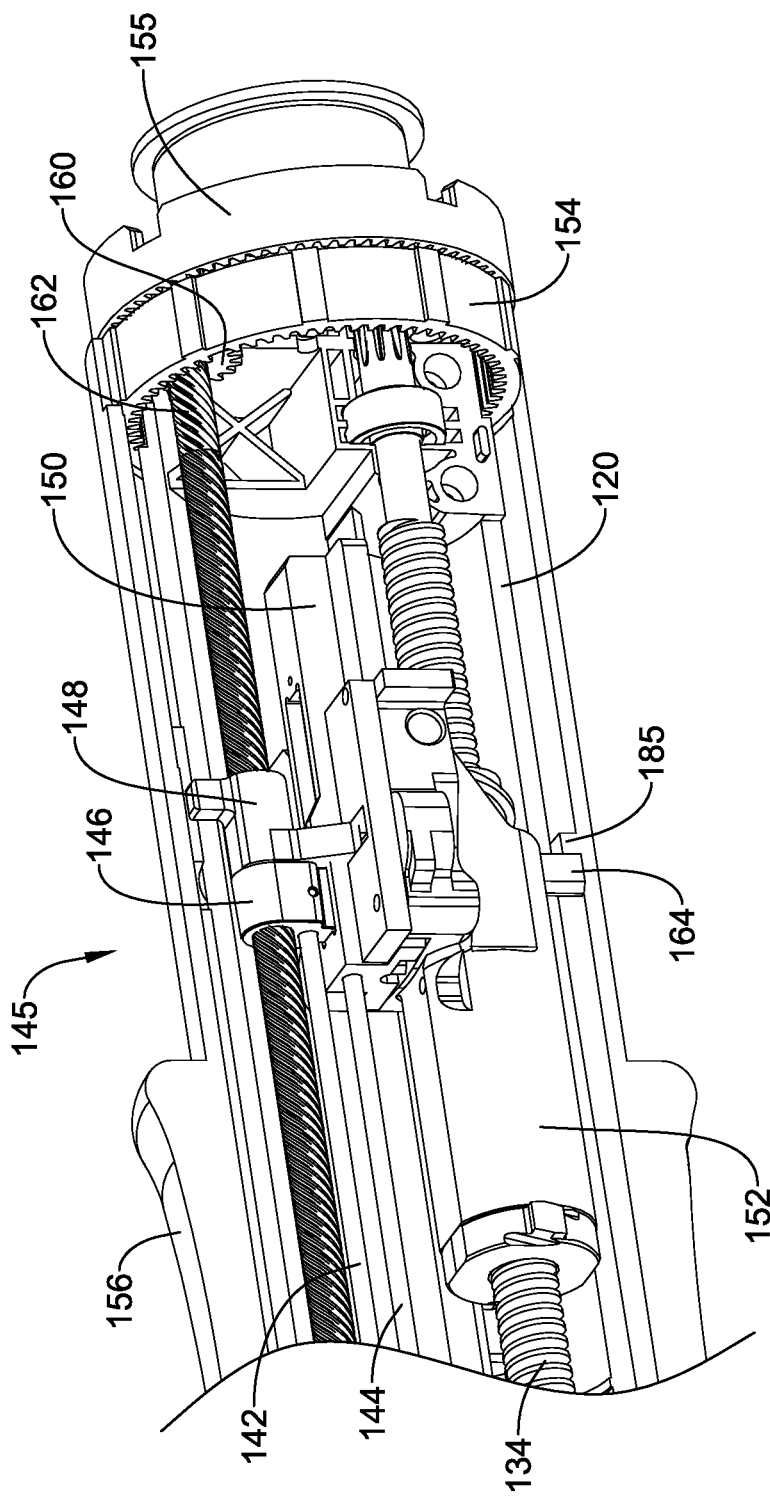
FIGS. 15-17 illustrate an example of coordinated movement of selected components within the example medical device handle.

As most easily seen in FIG. 15, for example, the medical device handle 18 may include a rotatable ring 155 with internal teeth that are configured to engage with teeth on a gear (not visible) coupled to the lead screw 134. The rotatable ring 155 may be operably coupled to the rotatable control knob 122 so that rotation of the rotatable control knob 122 results in analogous motion of the rotatable ring 155 and thus the lead screw 134. The medical device handle 18 may include a rotatable ring 154 with internal teeth that are configured to engage with teeth on a gear 160 coupled to the lead screw 162. The rotatable ring 154 may be operably coupled to the tubular collar member 156 so that rotation of the tubular collar member 156 results in analogous motion of the rotatable ring 154 and thus the lead screw 162. In some embodiments, the lead screw 162 may extend through and/or be engaged with the first sliding member 146, wherein rotation of the lead screw 162 results in proximal axial translation of the first sliding member 146 relative to the second sliding member 150 and/or the carriage member 152.

Turning back to FIGS. 10-12, the medical device handle 18 may generally be configured for coordinated movement of multiple structures of the medical device system 10. For example, the medical device handle 18 maybe configured to allow a user to move the outer sheath 12 (e.g., relative to the inner catheter 14), to move the plurality of actuator members 84, and/or to move the pin release mandrel 92. Moreover, the medical device handle 18 is configured so that the appropriate structure can be moved at the appropriate time during the intervention so that the medical implant 16 can be delivered in an efficient manner.

Figure 10:
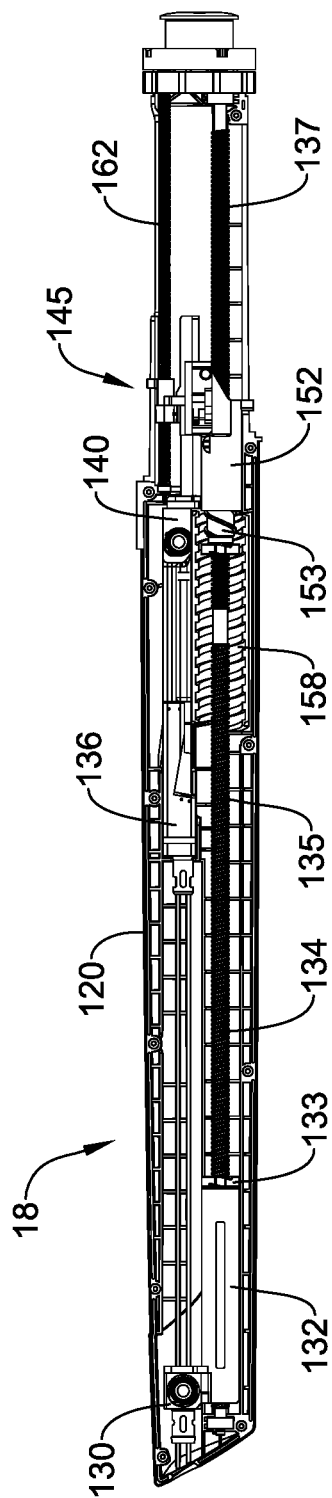
FIGS. 10-12 illustrate an example of coordinated movement of selected components within the example medical device handle.
Figure 11:
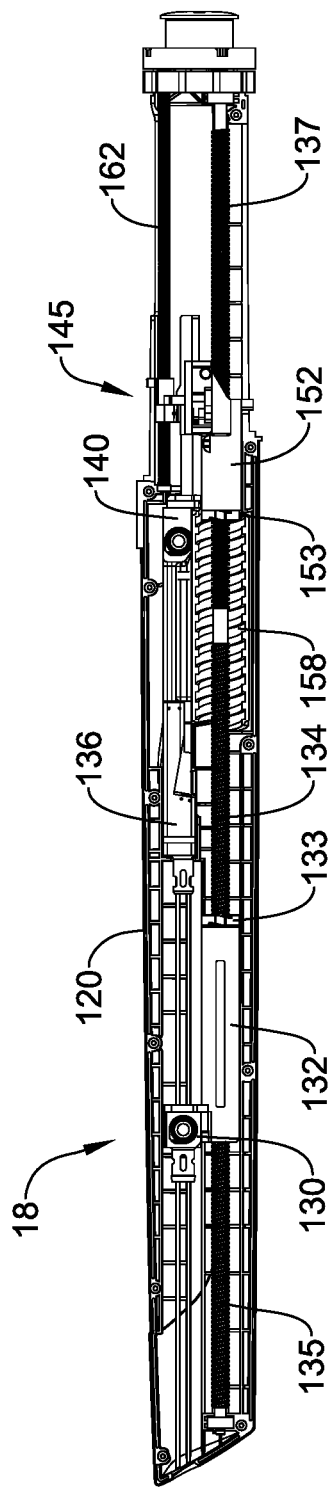
Figure 12:
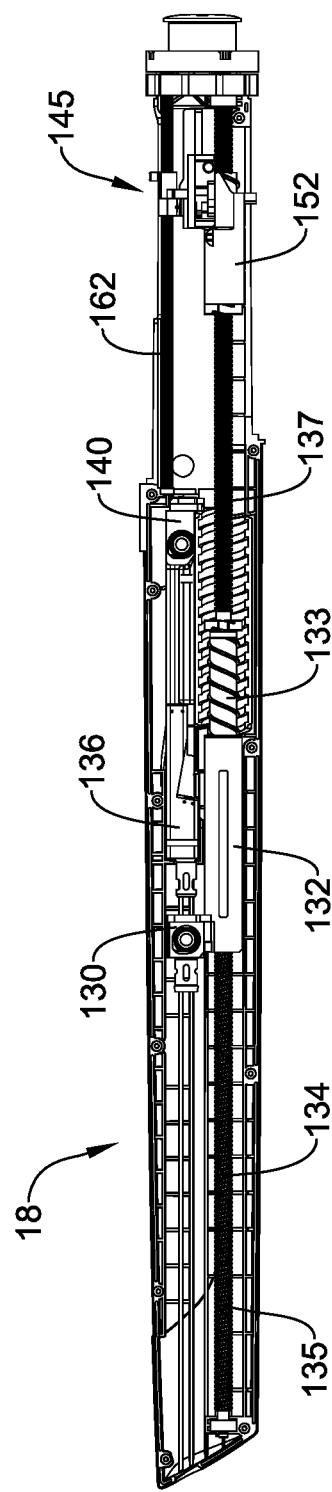
Figure 13:
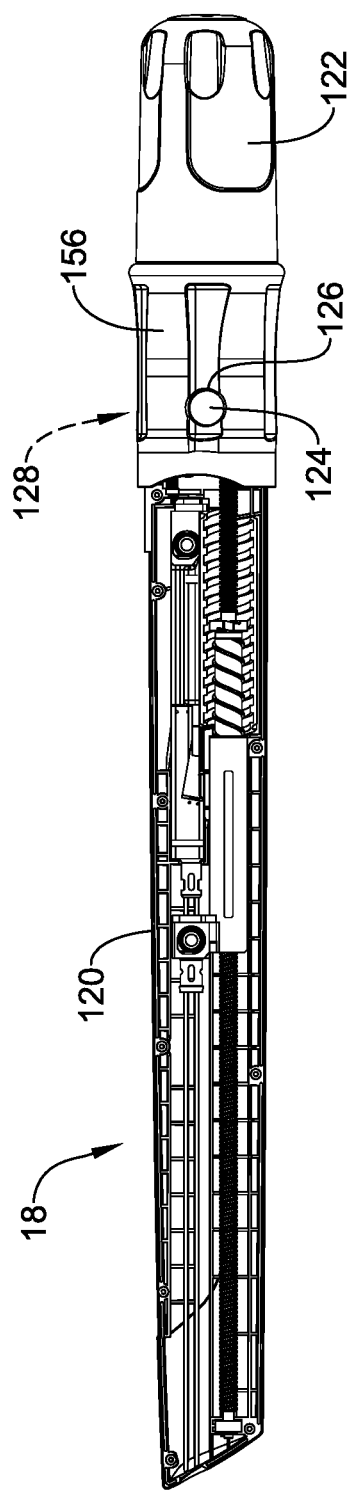
FIGS. 13-14 illustrate selected components of the example medical device handle associated with a release process of an example medical implant.

To help facilitate the coordinated movement, the medical device handle 18 may include a lost motion barrel 158. The lost motion barrel 158 may be configured to engage the sheath carriage 132 and/or the carriage member 152 and/or screws associated with the sheath carriage 132 and/or the carriage member 152 at different times during the intervention to stop motion (e.g., create "lost motion" of the appropriate carriage). FIGS. 10-12 illustrate some of the coordinated motion achieved by the medical device handle 18. It should be noted that some elements of the medical device system 10 are not shown in FIGS. 10-12 for clarity. For example, FIG. 10 illustrates a first state for the medical device handle 18 wherein the outer sheath 12 is extended distally relative to the inner catheter 14, the medical implant 16, and/or the handle housing 120 so as to fully sheath (e.g., contain) the medical implant 16 within the lumen of the outer sheath 12. While in this state, the sheath carriage 132 is positioned adjacent to the distal end of the medical device handle 18. In addition, a rod screw 153 associated with the carriage member 152 is extended distally from the carriage member 152 and positioned within the lost motion barrel 158. Upon rotation of the rotatable control knob 122 (e.g., in the clockwise direction), the lead screw 134 begins to rotate. Rotation of the lead screw 134 causes the sheath carriage 132 to move along the lead screw 134 in the proximal direction, resulting in proximal movement of the outer sheath 12 relative to the inner catheter 14, the medical implant 16, and/or the handle housing 120 (e.g., "unsheathing" the medical implant 16). This initial rotation of the lead screw 134 may also cause the rod screw 153 to rotate. This may be because, for example, a knob or projection (not shown) on the rod screw 153 may be engaged with a helical thread disposed along an interior surface of the lost motion barrel 158. However, because the rod screw 153 is spaced from the carriage member 152, it does not exert a force onto the carriage member 152. Thus, initial motion of the rotatable control knob 122 does not result in axial translation of the carriage member 152 and, instead, only results in axial translation of the sheath carriage 132 and rotation (and/or translation) of the rod screw 153.

Eventually, the rod screw 153 (e.g., the knob formed therein) reaches an essentially linear thread or pathway formed at the proximal end of the lost motion barrel 158. The linear thread allows the rod screw 153 to axially translate proximally along the lead screw 134 to a position where the rod screw 153 contacts (e.g., is threaded within and abuts) the carriage member 152. In doing so, the rod screw 153 can contact and axially translate the carriage member 152 proximally. Accordingly, further rotation of the lead screw 134 not only causes the sheath carriage 132 to move proximally but also causes the carriage member 152 to move proximally, as shown in FIG. 11 for example.

When the sheath carriage 132 reaches the lost motion barrel 158, a sheath carriage screw 133 of the sheath carriage 132 enters the lost motion barrel 158, as shown in FIG. 12 for example. This may occur in a manner similar to how the rod screw 153 threads and unthreads with the helical thread formed along the lost motion barrel 158. For example, while the sheath carriage 132 is translating axially, the sheath carriage screw 133 may follow an essentially linear thread or pathway formed along and/or adjacent to the lost motion barrel 158. Upon reaching the lost motion barrel 158, the sheath carriage screw 133 (e.g., a knob or projection formed thereon) may shift into engagement with the helical thread within the lost motion barrel 158 and rotate. This rotation "unthreads" the sheath carriage screw 133 from the sheath carriage 132. Accordingly, additional rotation of the lead screw 134 results in continued axial translation proximally of the carriage member 152 while motion of the sheath carriage 132 ceases.

In at least some embodiments, the lead screw 134 has a plurality of portions, for example a first portion 135 and a second portion 137, each with a differing pitch to its thread relative to one another. This may allow the sheath carriage 132 and/or the carriage member 152 to travel at different rates along lead screw 134. For example, the pitch of lead screw 134 along which the sheath carriage 132 translates may be generally more spaced or slanted than at positions adjacent to the carriage member 152. Accordingly, the coordinated movement of the sheath carriage 132 and/or the carriage member 152 also may be configured so that the sheath carriage 132 translates along the lead screw 134 at a greater rate than the carriage member 152. Other configurations are contemplated where the above-mentioned configuration is reversed as well as further configurations where the pitch of lead screw 134 is essentially constant or includes a number of different pitch regions.

Sufficient proximal retraction of the carriage member 152, for example as shown in FIG. 12, may result in the plurality of actuator members 84 being sufficiently retracted so that the post members 72 can engage and lock with the buckle members 76. When the clinician is satisfied that locking is complete (e.g., after verification via an appropriate visualization technique), the clinician may proximally retract the pin release mandrel 92 in order to pull the release pins 88 to disconnect and/or detach the plurality of actuator members 84 from the post members 72 (and subsequently detaching the coupler 78 from the buckle members 76), thereby leaving the medical implant 16 in the "released" configuration.

FIGS. 13-17 illustrate selected aspects of a release process for the medical implant 16 and/or selected components of the medical device system 10 involved in the release process. To initiate release of the medical implant 16 after actuating and/or translating the medical implant 16 and/or the tubular anchor member 70 into the "deployed" configuration, the button mechanism 124 may be depressed, actuated, and/or translated radially inward relative to the longitudinal axis of the handle housing 120 from the first position to the second position while the tubular collar member 156 is in the first orientation, thereby disengaging the button mechanism 124 from the first aperture 126. Depressing, actuating, and/or translating the button mechanism 124 from the first position to the second position may unlock the tubular collar member 156, thereby permitting relative movement (e.g., rotational movement, etc.) of the tubular collar member 156 with respect to the handle housing 120.

Figure 14:
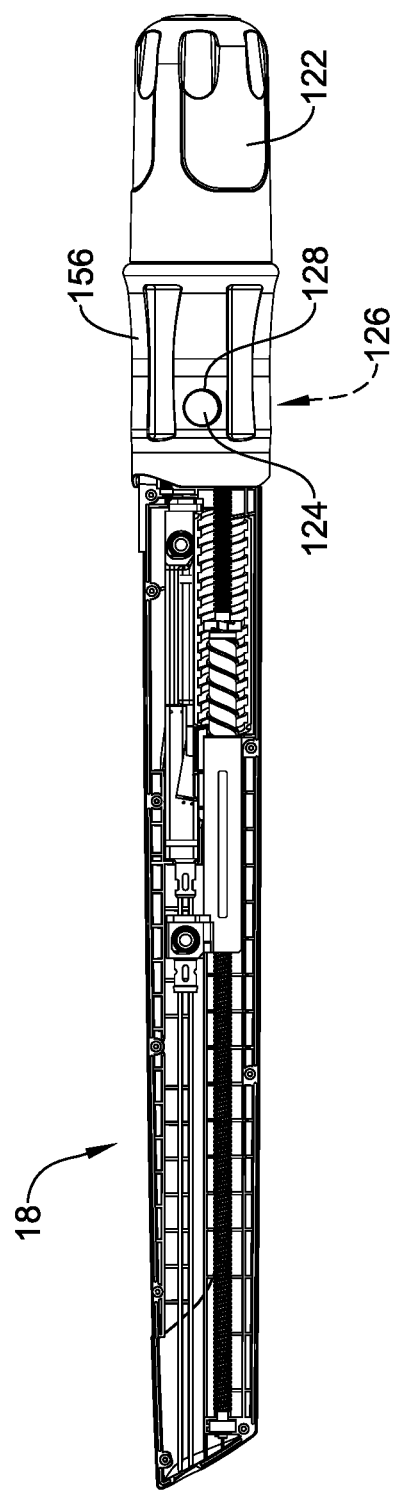

Next, the tubular collar member 156 may be rotated about and/or relative to the handle housing 120 from the first orientation (seen in FIG. 13, for example) to the second orientation (seen in FIG. 14 for example). In some embodiments, when the tubular collar member 156 is in the first orientation, the locking element 148 may physically engage the second sliding member 150 and/or the carriage member 152, thereby locking the first sliding member 146, the second sliding member 150, and the carriage member 152 with respect to longitudinal and/or axial movement therebetween when the locking element 148 is in a locked orientation, as seen in FIG. 15 for example. When the locking element 148 is in the locked orientation, the first sliding member 146, which may be positioned within a slot or groove within the second sliding member 150, may be secured and/or disposed between the second sliding member 150 and the locking element 148 in a first position at and/or adjacent a distal end of the slot or groove within the second sliding member 150, thereby preventing axial and/or sliding movement of the first sliding member 146 relative to the second sliding member 150, the carriage member 152, and/or the handle housing 120.

Figure 16:
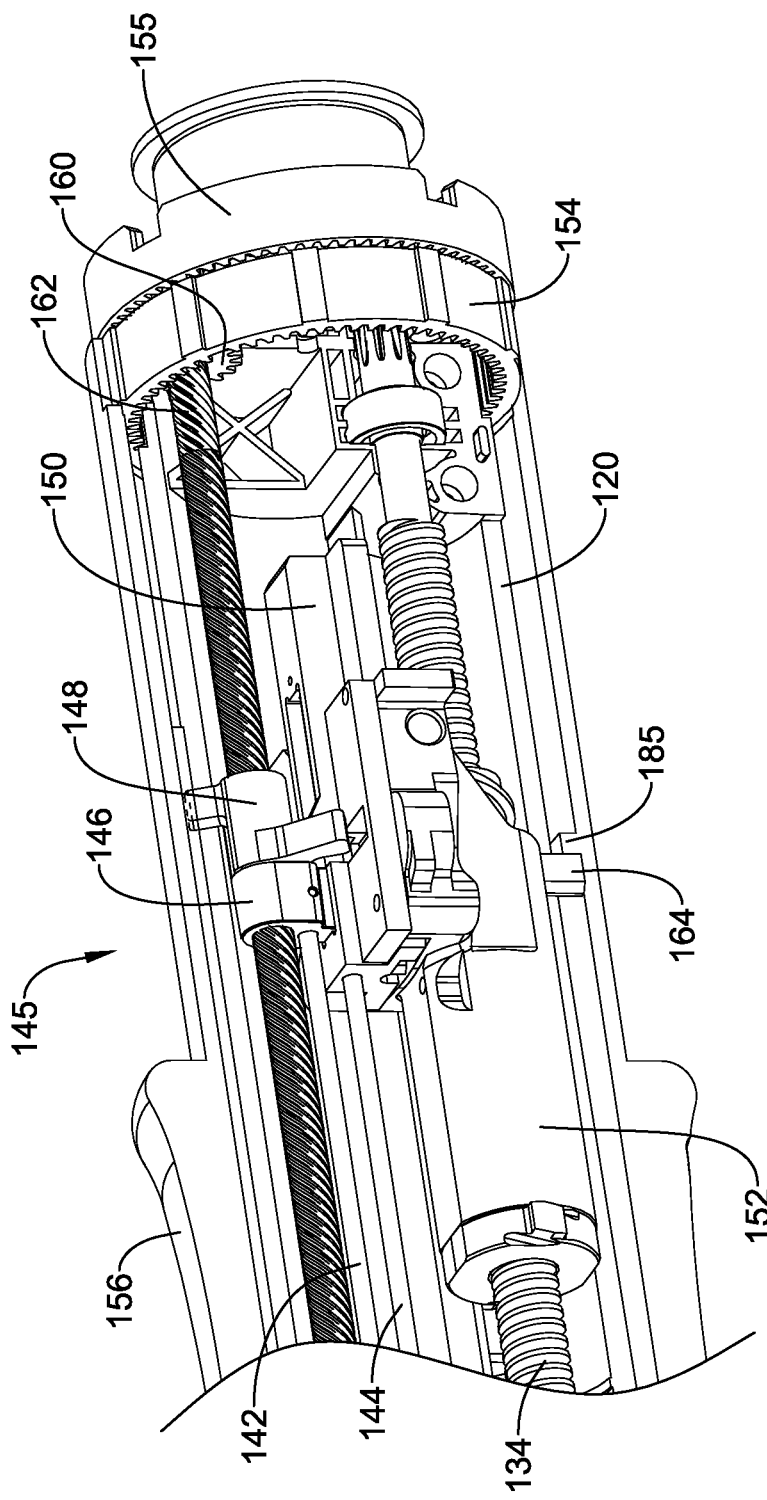

Initial rotation of the tubular collar member 156 about the longitudinal axis and/or away from the first orientation may cause a protrusion 188 (see FIG. 7) extending radially inwardly from the inner surface of the tubular collar member 156 to contact the portion of the locking element 148 that was engaged with the first internally-facing longitudinal slot 187 and rotate the locking element 148 with respect to the lead screw 162, the first sliding member 146, the second sliding member 150, and/or the handle housing 120, etc., out of engagement with the second sliding member 150 and/or the carriage member 152 to an unlocked orientation, as seen in FIG. 16 for example. After rotating the locking element 148 out of engagement with the second sliding member 150 and/or the carriage member 152 and/or to the unlocked orientation, the first sliding member 146 may be longitudinally and/or axially movable proximally relative to the second sliding member 150 and/or the carriage member 152 from the first position toward a second position at and/or adjacent a proximal end of the slot or groove in the second sliding member 150. In some embodiments, after releasing the first sliding member 146 and the second sliding member 150 from the carriage member 152, tension on the at least one actuator member 84 may be released until the first sliding member 146 re-engages the second sliding member 150 at a proximal end of a slot formed in the second sliding member 150, as described below.

Further rotation of the tubular collar member 156 about and/or relative to the handle housing 120 may cause the lead screw 162 to turn, thereby translating and/or axially moving the first sliding member 146 proximally within the slot or groove in the second sliding member 150 (and/or relative to the second sliding member 150) from the first position to the second position. In at least some embodiments, when the first sliding member 146 is in the second position, the first sliding member 146 abuts a portion of the second sliding member 150. In some embodiments, when the first sliding member 146 is in the second position, the first sliding member 146 abuts a distally-facing surface within the slot or groove of the second sliding member 150. Proximal translation and/or movement of the first sliding member 146 from the first position to the second position may retract and/or pull the pin release mandrel 92 and/or the release pins 88 to disconnect and/or disengage the release pins 88 from the medical implant 16, the locking mechanism(s), and/or the post member(s) 72, thereby irreversibly detaching the at least one actuator member 84 from the medical implant 16.

Figure 17:
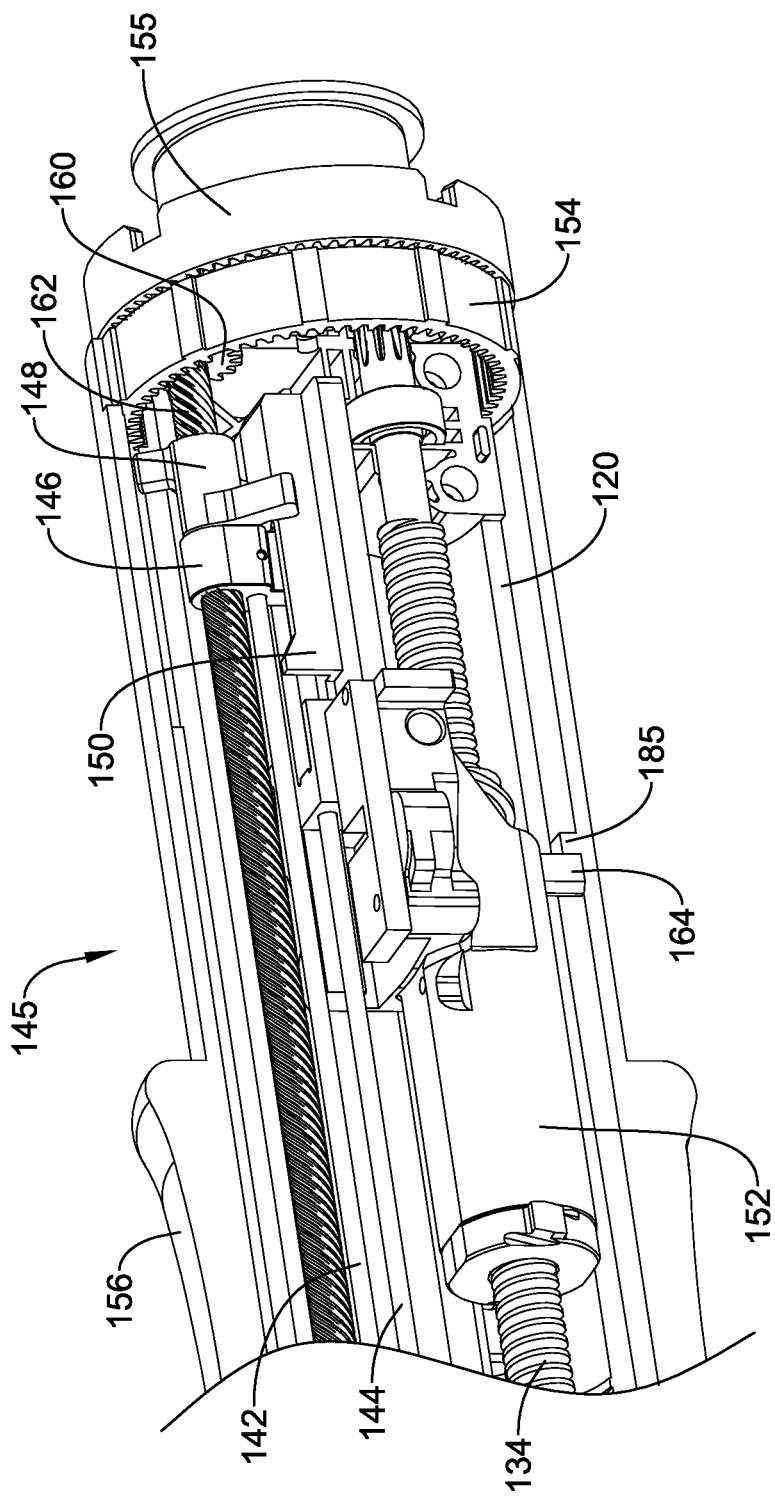

In some embodiments, after the first sliding member 146 is in the second position within the slot or groove in the second sliding member 150, further and/or partial rotation of the tubular collar member 156 about and/or relative to the handle housing 120 may move and/or axially translate the second sliding member 150 proximally relative to the carriage member 152 and/or the handle housing 120, as seen in FIG. 17. In some embodiments, after the first sliding member 146 is in the second position within the slot or groove in the second sliding member 150, further and/or partial rotation of the tubular collar member 156 about and/or relative to the handle housing 120 may move and/or axially translate the first sliding member 146 and the second sliding member 150 proximally together and/or simultaneously relative to the carriage member 152 and/or the handle housing 120. Axial translation of the second sliding member 150 proximally relative to the carriage member 152 may proximally retract the at least one actuator member 84 from the medical implant 16, the locking mechanism(s), and/or the post member(s) 72.

Upon achieving the second orientation of the tubular collar member 156, the button mechanism 124 may extend, actuate, and/or translate from the second position radially outward to the first position within the second aperture 128, and may re-engage and/or lock the tubular collar member 156 with respect to the handle housing 120, as seen in FIG. 14 for example. Re-engagement of the button mechanism 124 with the tubular collar member 156 in the second orientation may indicate to a user that the release process has been completed and/or that the medical implant 16 has been released from the medical device system 10.

The materials that can be used for the various components of the medical device system 10 (and/or other systems disclosed herein) and the various elements thereof disclosed herein may include those commonly associated with medical devices. For simplicity purposes, the following discussion makes reference to the delivery system and/or the medical implant 16. However, this is not intended to limit the devices and methods described herein, as the discussion may be applied to other elements, members, components, or devices disclosed herein, such as, but not limited to, the tubular anchor member 70, the actuator member 84, the locking mechanism, the post member 72, the buckle member 76, and/or elements or components thereof.

In some embodiments, the delivery system and/or the medical implant 16, and/or components thereof (such as, but not limited to, the tubular anchor member 70, the locking mechanisms, the actuator members 84, etc.), may be made from a metal, metal alloy, polymer (some examples of which are disclosed below), a metal-polymer composite, ceramics, combinations thereof, and the like, or other suitable material. Some examples of suitable metals and metal alloys include stainless steel, such as 444V, 444L, and 314LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R44035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R44003 such as ELGILOY®, PHYNOX®, and the like); platinum enriched stainless steel; titanium; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear than the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of the delivery system and/or the medical implant 16, and/or components thereof, may also be doped with, made of, or otherwise include a radiopaque material. Radiopaque materials are understood to be materials capable of producing a relatively bright image on a fluoroscopy screen or another imaging technique during a medical procedure. This relatively bright image aids a user in determining the location of the delivery system and/or the medical implant 16. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the delivery system and/or the medical implant 16 to achieve the same result.

In some embodiments, a degree of Magnetic Resonance Imaging (MRI) compatibility is imparted into the medical implant 16. For example, the delivery system and/or the medical implant 16, and/or components or portions thereof, may be made of a material that does not substantially distort the image and create substantial artifacts (e.g., gaps in the image). Certain ferromagnetic materials, for example, may not be suitable because they may create artifacts in an MRI image. The delivery system and/or the medical implant 16, or portions thereof, may also be made from a material that the MRI machine can image. Some materials that exhibit these characteristics include, for example, tungsten, cobalt-chromium-molybdenum alloys (e.g., UNS: R44003 such as ELGILOY®, PHYNOX®, and the like), nickel-cobalt-chromium-molybdenum alloys (e.g., UNS: R44035 such as MP35-N® and the like), nitinol, and the like, and others.

In some embodiments, a sheath or covering (not shown) may be disposed over portions or all of the delivery system and/or the medical implant 16. The sheath may be made from a polymer or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyetherester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

It should be understood that this disclosure is, in many respects, only illustrative. Changes may be made in details, particularly in matters of shape, size, and arrangement of steps without exceeding the scope of the invention. This may include, to the extent that it is appropriate, the use of any of the features of one example embodiment being used in other embodiments. The invention's scope is, of course, defined in the language in which the appended claims are expressed.

What is claimed is:

1. A medical device handle for percutaneous delivery of a medical implant from a tubular member extending distally from the medical device handle, comprising:
   a handle housing having a longitudinal axis extending from a proximal end of the handle housing to a distal end of the handle housing, the handle housing including a cavity disposed within the handle housing; and
   a carriage assembly disposed within the cavity and operatively connected to the tubular member and the carriage assembly is further configured to be operatively connected to the medical implant, the carriage assembly being longitudinally movable between a distal position and a proximal position by rotation of a control knob with respect to the handle housing, the control knob being disposed around the proximal end of the handle housing;
   wherein the carriage assembly includes a carriage member, a first sliding member, a second sliding member, and a lock configured to releasably fix the first sliding member and the second sliding member relative to the carriage member;
   wherein the lock is rotatable relative to the handle housing.

2. The medical device handle of claim 1, further including a tubular collar member disposed around a proximal portion of the handle housing, the tubular collar member being rotatable about the handle housing.

3. The medical device handle of claim 2, wherein the lock physically engages the carriage member.

4. The medical device handle of claim 3, wherein rotating the tubular collar member about the longitudinal axis rotates the lock out of engagement with the carriage member.

5. The medical device handle of claim 4, wherein after rotating the lock out of engagement with the carriage member, the first sliding member is longitudinally movable with respect to the second sliding member.

6. The medical device handle of claim 5, wherein the first sliding member is movable proximally, from a first position to a second position, relative to the second sliding member.

7. The medical device handle of claim 6, wherein in the second position, the first sliding member abuts a portion of the second sliding member.

8. The medical device handle of claim 6, wherein after rotating the lock out of engagement with the carriage member, further rotation of the tubular collar member moves the first sliding member proximally relative to the second sliding member.

9. The medical device handle of claim 8, wherein after the first sliding member is in the second position, further rotation of the tubular collar member moves the second sliding member proximally relative to the carriage member.

10. The medical device handle of claim 9, wherein after the first sliding member is in the second position, further rotation of the tubular collar member moves both the first sliding member and the second sliding member proximally relative to the carriage member.

11. The medical device handle of claim 1, wherein the second sliding member includes at least one actuator member extending distally therefrom to the medical implant, wherein movement of the carriage assembly from the distal position toward the proximal position places the at least one actuator member in tension.

12. The medical device handle of claim 11, wherein after releasing the first sliding member and the second sliding member from the carriage member, the carriage assembly releases tension on the at least one actuator member until the first sliding member re-engages the second sliding member at a proximal end of a slot formed in the second sliding member.

13. A medical device handle for percutaneous delivery of a medical implant from a tubular member extending distally from the medical device handle, comprising:
a handle housing having a longitudinal axis extending from a proximal end of the handle housing to a distal end of the handle housing, the handle housing including a cavity disposed within the handle housing;
a carriage assembly disposed within the cavity and operatively connected to the tubular member and the carriage assembly is further configured to be operatively connected to the medical implant, the carriage assembly being longitudinally movable between a distal position and a proximal position by rotation of a control knob with respect to the handle housing, the control knob being disposed around the proximal end of the handle housing;
wherein the carriage assembly includes a carriage member, a first sliding member, a second sliding member, and a lock configured to releasably fix the first sliding member and the second sliding member relative to the carriage member, the lock being rotatable relative to the handle housing; and
a tubular collar member disposed around a proximal portion of the handle housing, the tubular collar member being rotatable about the handle housing;
wherein the handle housing includes a button mechanism configured to engage the tubular collar member in a first orientation of the tubular collar member relative to the handle housing when the first sliding member and the second sliding member are fixed to the carriage member by the lock, and the button mechanism is configured to engage the tubular collar member in a second orientation of the tubular collar member relative to the handle housing when the first sliding member and the second sliding member are not fixed to the carriage member by the lock.

14. The medical device handle of claim 13, wherein at least a portion of the button mechanism extends radially outward from the handle housing.

15. The medical device handle of claim 13, wherein when the button mechanism is engaged with the tubular collar member in the first orientation of the tubular collar member, the tubular collar member is prevented from rotating about the handle housing.

16. The medical device handle of claim 13, wherein when the button mechanism is engaged with the tubular collar member in the second orientation of the tubular collar member, the tubular collar member is prevented from rotating about the handle housing.

17. A medical device system, comprising:
a handle housing including a longitudinally movable carriage assembly disposed therein, the carriage assembly including a carriage member, a first slider member, a second slider member, and a lock releasably fixing the first slider member and the second slider member relative to the carriage member, the lock being rotatable with respect to the handle housing;
a tubular member extending distally from the handle housing;
a replacement heart valve deployable from a distal end of the tubular member;
at least one actuator member extending distally from the carriage assembly through the tubular member to the replacement heart valve, the at least one actuator member being releasably attached to the replacement heart valve; and
a tubular collar member disposed around and rotatable with respect to the handle housing, the tubular collar member being configured to release the first sliding member and the second sliding member from the carriage member upon rotation about the handle housing.

18. The medical device system of claim 17, wherein partial rotation of the tubular collar member about the handle housing translates the first sliding member proximally relative to the second sliding member until the first sliding member abuts a portion of the second sliding member, thereby irreversibly detaching the at least one actuator member from the replacement heart valve.

19. The medical device system of claim 18, wherein partial rotation of the tubular collar member about the handle housing after the first sliding member abuts the portion of the second sliding member translates the second sliding member proximally relative to the carriage member.

20. The medical device system of claim 19, wherein translation of the second sliding member proximally relative to the carriage member proximally retracts the at least one actuator member from the replacement heart valve.

* * * * *